(12) United States Patent
Moshos et al.

(10) Patent No.: US 10,214,543 B2
(45) Date of Patent: Feb. 26, 2019

(54) SYNTHESIS OF CEPHALOSPORIN COMPOUNDS

(71) Applicant: MERCK SHARP & DOHME CORP., Rahway, NJ (US)

(72) Inventors: Kristos Adrian Moshos, Belmont, MA (US); Valdas Jurkauskas, Cambridge, MA (US); Giovanni Fogliato, Barzana (IT); Manuel Scanu, Milan (IT); Michele Benotti, Pavia (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/540,283

(22) PCT Filed: Dec. 18, 2015

(86) PCT No.: PCT/US2015/066781
§ 371 (c)(1),
(2) Date: Jul. 7, 2016

(87) PCT Pub. No.: WO2016/109259
PCT Pub. Date: Jul. 7, 2016

(65) Prior Publication Data
US 2018/0170949 A1    Jun. 21, 2018

Related U.S. Application Data

(60) Provisional application No. 62/097,857, filed on Dec. 30, 2014.

(51) Int. Cl.
*C07D 501/56* (2006.01)
*C07D 417/14* (2006.01)
*C07B 43/04* (2006.01)
*C07B 43/06* (2006.01)
*C07B 51/00* (2006.01)

(52) U.S. Cl.
CPC ............ *C07D 501/56* (2013.01); *C07B 43/04* (2013.01); *C07B 43/06* (2013.01); *C07B 51/00* (2013.01); *C07D 417/14* (2013.01)

(58) Field of Classification Search
None
See application file for complete search history.

(56) References Cited

U.S. PATENT DOCUMENTS

| | | |
|---|---|---|
| 3,720,669 A | 3/1973 | Breuer |
| 4,464,368 A | 8/1984 | O'Callaghan et al. |
| 5,359,058 A | 10/1994 | Verweij et al. |
| 5,401,734 A | 3/1995 | Yamanaka et al. |
| 7,129,232 B2 | 10/2006 | Ohki et al. |
| 7,192,943 B2 | 3/2007 | Yamanaka et al. |
| 8,906,898 B1 | 12/2014 | Hwang et al. |
| 2004/0132994 A1 | 7/2004 | Ohki et al. |
| 2005/0004094 A1 | 1/2005 | Yamanaka et al. |
| 2005/0096306 A1 | 5/2005 | Yamanaka et al. |
| 2007/0037786 A1 | 2/2007 | Ohki et al. |
| 2013/0065874 A1 | 3/2013 | Chandorkar et al. |
| 2013/0066065 A1 | 3/2013 | Vervest |
| 2014/0274958 A1 | 9/2014 | Lai et al. |
| 2014/0274999 A1 | 9/2014 | Lai et al. |
| 2016/0176897 A1 | 6/2016 | Moshos et al. |
| 2017/0129906 A1 | 5/2017 | Moshos et al. |
| 2017/0275300 A1* | 9/2017 | Waller ................. C07D 501/04 |

FOREIGN PATENT DOCUMENTS

| | | | |
|---|---|---|---|
| EP | 0064582 | 12/1985 | |
| EP | 1556389 | 3/2005 | |
| JP | 1135778 | 5/1989 | |
| WO | WO-2005027909 A1 * | 3/2005 | ........... C07D 501/00 |
| WO | WO2005027909 A1 | 3/2005 | |
| WO | WO2007119511 | 10/2007 | |
| WO | WO2014152763 A1 | 9/2014 | |
| WO | WO2016025813 | 2/2016 | |
| WO | WO2016025839 | 2/2016 | |
| WO | WO2016095860 | 6/2016 | |
| WO | WO2016100897 | 6/2016 | |
| WO | WO2016109259 | 7/2016 | |

OTHER PUBLICATIONS

Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18, WO.

Kenji Murano, Structural Requirements for the stability of novel cephalosporins to AMPC B-lactamase based on 3D-structure, Bioorganic and Medicinal Chemistry, Nov. 22, 2007, 2261-2275, 16, WO.

Vittorio Farina, et al., Palladium-catalyzed coupling between cephalosporin derivatives and unsaturated stannanes: A new ligand for palladium chemistry, Tetrahedron Letters, 1988, pp. 5739-5742., vol. 29, Issue 45.

PCT Search Report and Written Opinion for PCT/US2015/066781 dated Jul. 4, 2017; 5 pages.

* cited by examiner

*Primary Examiner* — Deepak R Rao
*Assistant Examiner* — Laura M Daniel
(74) *Attorney, Agent, or Firm* — J. Eric Thies; John C. Todaro

(57) ABSTRACT

Described herein are methods for the manufacture of ceftolozane and related compounds, as well as compositions comprising the same.

20 Claims, 5 Drawing Sheets

FIGURE 5

| Scale and Batch | Sub-stage | Peak 1 (% AUC) | Post-Peak 9 (% AUC) | Ceftolozane (% AUC) |
|---|---|---|---|---|
| 50 kg, A | Compound (Vb) (ceftolozane TFA crude) | 2.76 | 13.49 | 76.67 |
| | after passage through HP20L resin | 1.86 | 0.21 | 93.84 |
| 50 kg, B | Compound (Vb) (ceftolozane TFA crude) | 2.80 | 12.67 | 78.09 |
| | after passage through HP20L resin | 1.79 | 0.20 | 94.56 |
| 50 kg, C | Compound (Vb) (ceftolozane TFA crude) | 2.86 | 12.81 | 79.78 |
| | after passage through HP20L resin | 2.34 | 0.22 | 94.62 |
| 50 kg, D | Compound (Vb) (ceftolozane TFA crude) | 2.45 | 13.46 | 77.18 |
| | after passage through HP20L resin | 2.38 | 0.33 | 92.87 |
| 50 kg, E | Compound (Vb) (ceftolozane TFA crude) | 2.34 | 13.10 | 78.29 |
| | after passage through HP20L resin | 2.71 | 0.20 | 93.89 |
| 50 kg, F | Compound (Vb) (ceftolozane TFA crude) | 2.45 | 13.35 | 76.96 |
| | after passage through HP20L resin | 2.80 | 0.33 | 93.11 |
| 170 kg, G | Compound (Vb) (ceftolozane TFA crude) | 3.55 | 16.32 | 75.57 |
| | after passage through HP20L resin | 2.28 | 0.13 | 94.75 |

SYNTHESIS OF CEPHALOSPORIN COMPOUNDS

1. CROSS REFERENCE TO RELATED APPLICATIONS

This application claims the benefit under 35 U.S.C. § 119(e) of U.S. Provisional Application No. 62/097,857, filed Dec. 30, 2014, the content of which is incorporated herein in its entirety by reference thereto.

2. TECHNICAL FIELD

This disclosure relates to the synthesis of chemical compounds, including intermediates in the synthesis of cephalosporins such as ceftolozane.

3. BACKGROUND

Ceftolozane is a cephalosporin antibacterial agent of the beta-lactam class (β-lactams), also referred to as CXA-101, FR264205, or by chemical names such as (6R,7R)-5-thia-1-azabicyclo[4.2.0]oct-2-ene-carboxylic acid, 3-[[4-[[[(2-aminoethyl)amino]carbamoyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo; or (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of ceftolozane that can be formulated for intravenous administration or infusion:

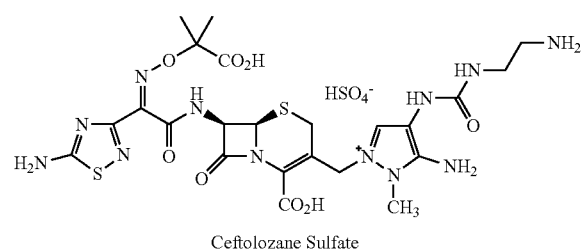

Ceftolozane Sulfate

Ceftolozane sulfate is also referred to as: 1H-Pyrazolium, 5-amino-4-[[[(2-aminoethyl)amino]carbonyl]amino]-2-[[(6R,7R)-7-[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-,sulfate (1:1); or 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate. Ceftolozane can be obtained as disclosed in U.S. Pat. No. 7,129,232, as well as in Toda et al., "Synthesis and SAR of novel parenteral anti-pseudomonal cephalosporins: Discovery of FR264205," *Bioorganic & Medicinal Chemistry Letters*, 18, 4849-4852 (2008), incorporated herein by reference. The antibacterial activity of ceftolozane is believed to result from its interaction with penicillin binding proteins (PBPs) to inhibit the biosynthesis of the bacterial cell wall which acts to stop bacterial replication.

There is a need for methods and improved processes of preparing compound (VI) and appropriate intermediate compounds to afford reproducibly high quality pharmaceutically acceptable ceftolozane salts such as compound (VI) on a commercial scale.

4. SUMMARY

The synthesis of ceftolozane sulfate compound (VI) is known in the art and can be prepared from the intermediate compounds (III) and (IV) according to the method depicted in, e.g., FIG. 1 (U.S. Pat. Nos. 7,192,943 and 7,129,232, as well as Toda et al., "Synthesis and SAR of novel parenteral anti-pseudomonal cephalosporins: Discovery of FR264205," *Bioorganic & Medicinal Chemistry Letters*, 18, 4849-4852 (2008)).

It has now been discovered that compound (VI) can be prepared according to the process depicted in, e.g., Scheme 1 and FIG. 2, and described herein, for example, as Method 1 (FIG. 3) and Method 2 (FIGS. 4 and 5). The invention of Method 1 is based in part on the discovery that the ratio of a compound of formula (IV'), e.g., compound (IV), to a compound of formula (III'), e.g., compound (III), during the coupling reaction can be reduced to about 1.2:1 without lowering the yield, thereby reducing the economic and environmental effects of the reaction.

Ceftolozane sulfate, compound (VI), can be prepared from a compound of formula (Vb'), e.g., compound (Vb), according to the method depicted, e.g., in FIGS. 4 and 5 and described herein as Method 2. The invention of Method 2 is based in part on the discovery that control of pH and filtration through a hydrophobic resin reduces the impurities in the process to obtain compound (VI).

In one aspect, provided herein is a method of making a compound of formula (V'):

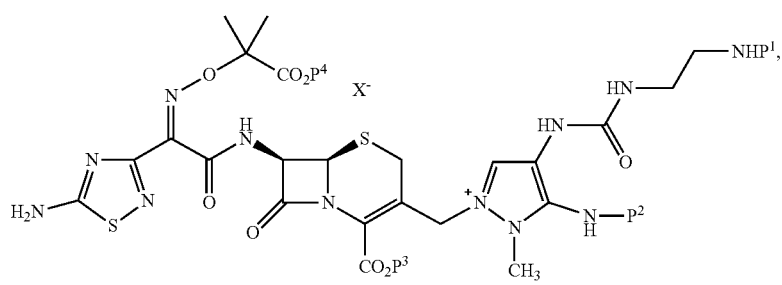

comprising admixing a compound of formula (III'):

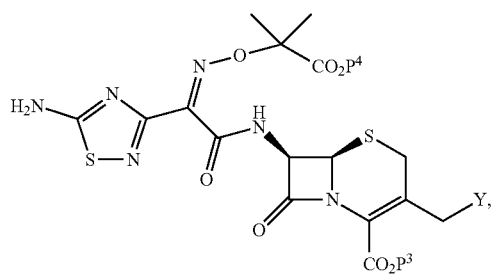

and a compound of formula (IV'):

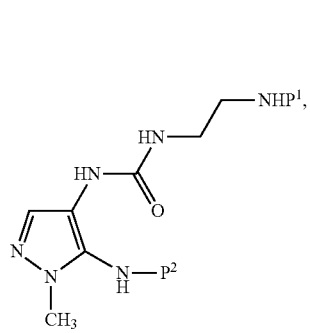

in a solvent to provide a compound of formula (V'), wherein
P¹ and P² are each independently an acid-labile nitrogen protecting group,
P³ and P⁴ are each independently an acid-labile oxygen protecting group,
X⁻ is a pharmaceutically acceptable salt,
Y is Cl or Br, such as Cl; and
the molar ratio of a compound of formula (IV') to a compound of formula (III') is from about 1.0:1 to about 1.3:1, preferably about 1.2:1.

In another aspect, provided herein is a method of making a compound of formula (V'):

comprising admixing a compound of formula (III'):

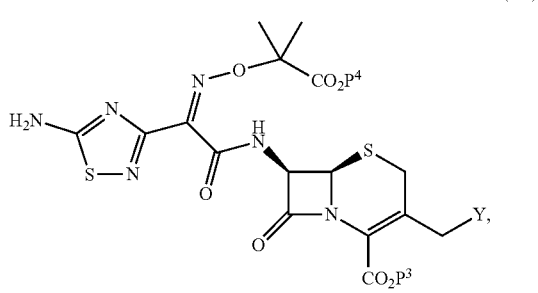

and a compound of formula (IV'):

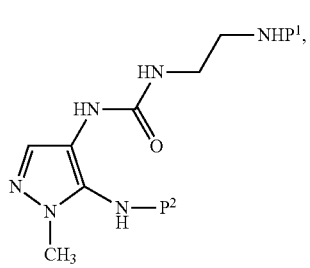

in a solvent to provide a compound of formula (V'), wherein
P¹ and P² are each independently an acid-labile nitrogen protecting group,
P³ and P⁴ are each independently an acid-labile oxygen protecting group,
X⁻ is a pharmaceutically acceptable salt,
Y is Cl, Br, or I, preferably Cl or Br, such as Cl; and
the temperature of the admixture is from about 25° C. to about 32° C.

In another aspect, provided herein is a method of making a compound of formula (V'):

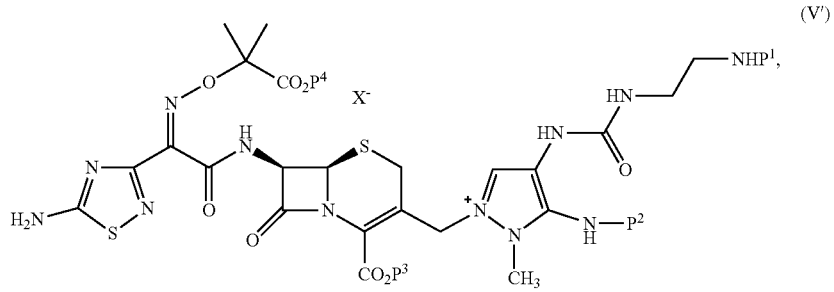

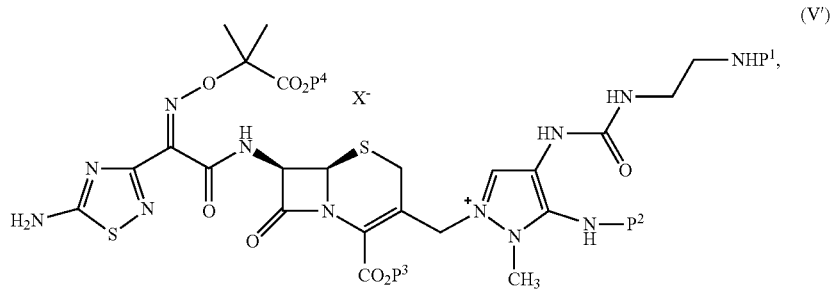

comprising admixing a compound of formula (III'):

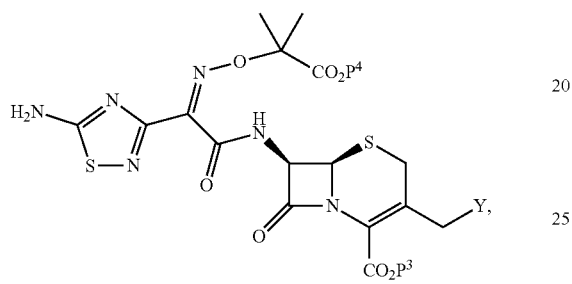

and a compound of formula (IV'):

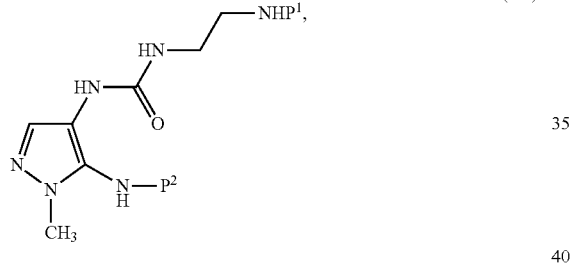

in a solvent to provide a compound of formula (V'), wherein $P^1$ and $P^2$ are each independently an acid-labile nitrogen protecting group, $P^3$ and $P^4$ are each independently an acid-labile oxygen protecting group, $X^-$ is a pharmaceutically acceptable salt, Y is Cl, Br, or I, preferably Cl or Br, such as Cl; and the solvent is purged with an inert gas, such as nitrogen, at from about 0.2 m³/h to about 1.2 m³/h per kilogram of the compound of formula (III').

In another aspect, provided herein is a method or a process of making the compound (V) (TATD-QUATE):

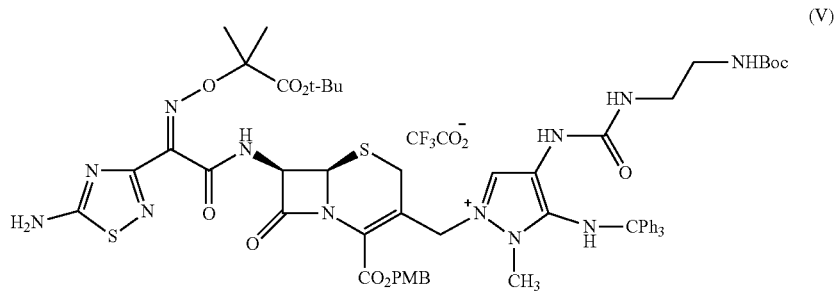

comprising admixing, e.g., reacting compound (III):

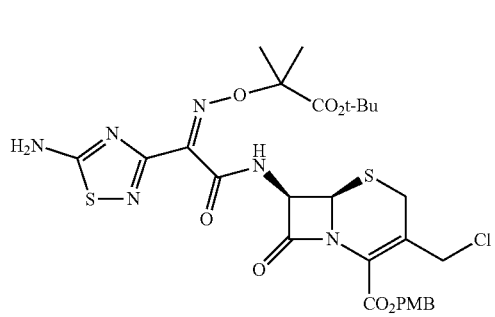

(III)

with compound (IV):

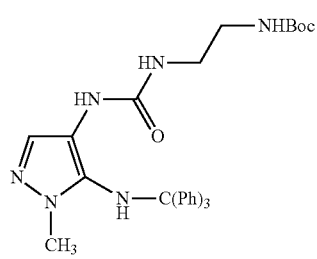

(IV)

under reaction conditions to provide, e.g., form compound (V).

In an embodiment, the ratio of compound (IV) to compound (III) is about 1.2:1.

In an embodiment, the reaction of compound (III) and compound (IV) further comprises formation of compound (IIIa):

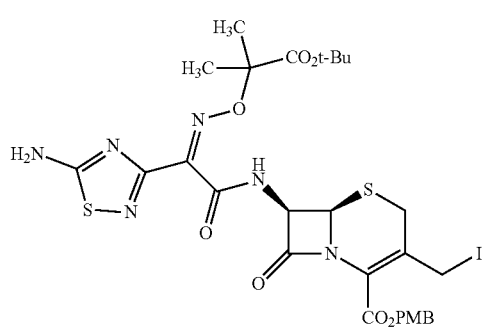

(IIIa)

In a further embodiment, the reaction is considered complete when less than about 5.0% of a compound (IIIa) remains as measured by high performance liquid chromatography (HPLC) (e.g., by the HPLC method provided in Example 4).

In one embodiment, the method of making a compound of formula (V') further comprises making a compound of formula (Vb'):

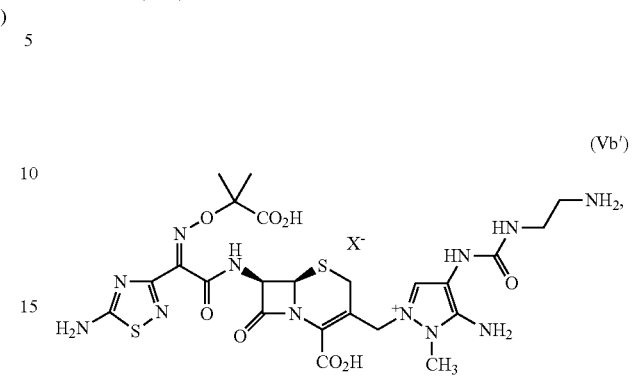

(Vb')

comprising contacting the compound of formula (V') with an acid of formula HX, at a temperature of from about 18° C. to about 22° C., to provide the compound of formula (Vb'), wherein HX is trifluoroacetic acid, hydrogen bromide, hydrogen chloride, hydrogen iodide, or methanesulfonic acid; and $X^-$ is trifluoroacetate, bromide, chloride, iodide, or methanesulfonate.

In an embodiment, the method further comprises treating the compound (V) with trifluoroacetic acid, such that compound (Vb) is formed:

(Vb)

In another aspect, provided herein is a method or a process of making the compound (VI) having the structure:

(VI)

comprising the steps of:
(a) forming a solution comprising compound (Vb):

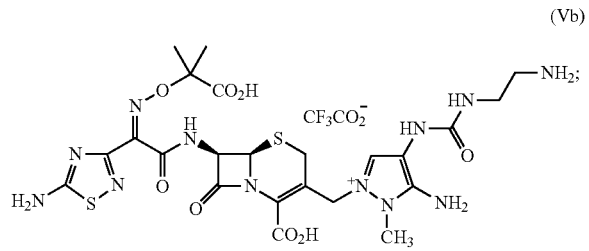

(b) adjusting the final pH of the solution formed in step (a) to between 1.2 and 2.0 and removing insoluble material;
(c) filtering the resulting solution of step (b) through a resin; and
(d) adding sulfuric acid to obtain compound (VI).

Maintenance of an appropriate pH of the solution at the various steps and using filtration, e.g., through a resin can greatly improve the purity of compound (VI) (ceftolozane sulfate).

5. BRIEF DESCRIPTION OF THE FIGURES

FIG. 5 is a table of data showing purity enhancement from compound (Vb) to compound (VI) using Method 2.

6. DETAILED DESCRIPTION

6.1. Definitions

Figure 1:
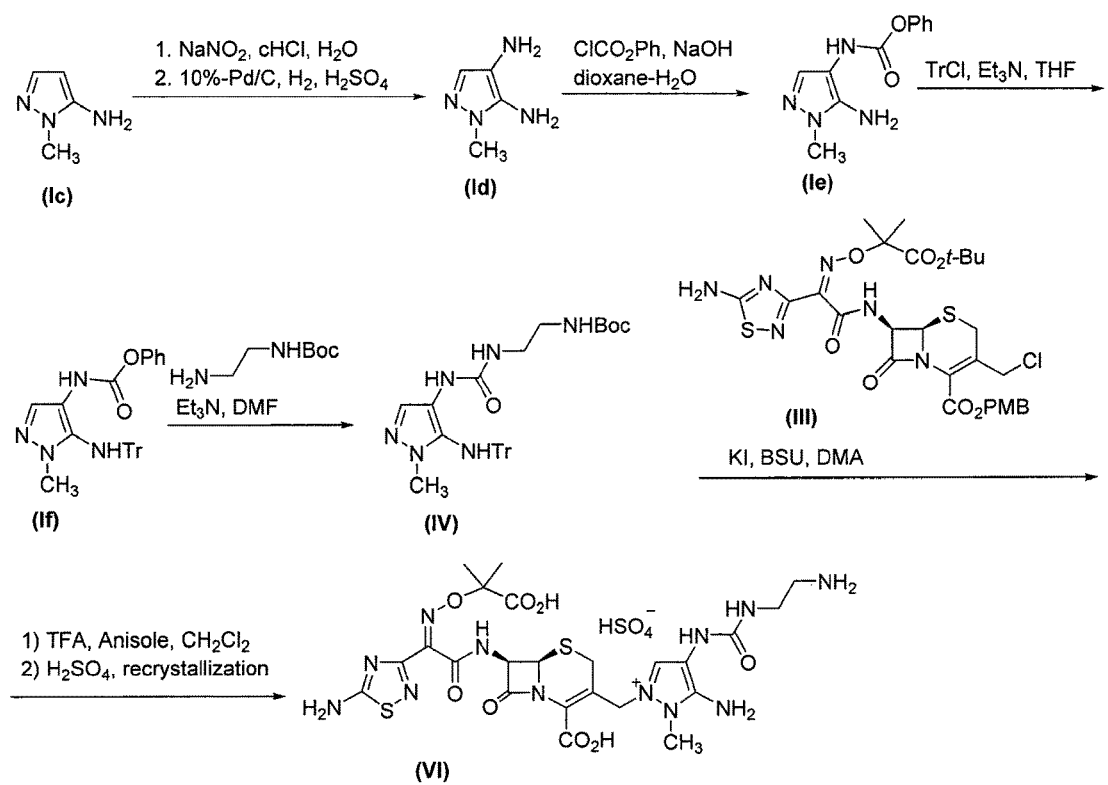
FIG. 1 shows a synthetic scheme to prepare compound (VI) (ceftolozane sulfate) (See, e.g., Bioorganic & Medicinal Chemistry Letters, 18, 4849-4852 (2008)).

Unless otherwise defined herein, scientific and technical terms used in connection with the present disclosure shall have the meanings that are commonly understood by those of ordinary skill in the art.

Abbreviations: ACN=acetonitrile; FID=flame ionization detector; GC=gas chromatography; HPLC=high performance liquid chromatography; KF=Karl-Fischer analysis; LOD=limit of detection; LOQ=limit of quantitation; PDA=photodiode array; TFA=trifluoroacetic acid.

The term "$C_{x-y}$ alkyl" refers to unsubstituted saturated hydrocarbon groups, including straight-chain alkyl and branched-chain alkyl groups that contain from x to y carbons in the chain. For example, $C_{1-6}$ alkyl is an alkyl group having two to six carbons. A "linear $C_{x-y}$ alkyl" refers to the "n" form of the alkyl group. For example, a "linear $C_6$ alkyl" is n-hexyl.

The term "hydroxyalkyl" refers to an alkyl group having one or more, e.g., one, two, or three or more, hydroxy (i.e., —OH) substituents.

As used herein, a "protecting group" is a moiety that masks the chemical reactivity of a functional group during one or more reactions. In an illustrative example, a nitrogen protecting group such as tert-butoxycarbonyl (i.e., tert-butyloxycarbonyl, Boc, or BOC) can be introduced at one step to mask the chemical reactivity of a protected nitrogen during one reaction then removed under acidic conditions to allow the formerly protected nitrogen to undergo reaction, e.g., alkylation. A protecting group can be any one known in the art, such as those described in Wuts, P. G. M.; Greene, T. W. Greene's Protective Groups in Organic Synthesis, 4$^{th}$ ed; John Wiley & Sons: Hoboken, N.J., 2007, or can be one that is developed in the future.

Oxygen and nitrogen protecting groups are known to those of skill in the art. Oxygen protecting groups include, but are not limited to, methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few), amides, cyclic imide derivatives, N-alkyl and N-aryl amines, benzyl amines, substituted benzyl amines, trityl amines, imine derivatives, and enamine derivatives, for example.

In some embodiments, the oxygen protecting group is a base-labile protecting group (i.e., one that can be removed under basic conditions), such as a methyl group when used as an ester to protect a carboxylic acid. In some embodiments, the oxygen protecting group is an acid-labile oxygen protecting group (i.e., one that can be removed under acid conditions), such as tert-butyl, 4-methoxybenzyl, or triphenylmethyl. In some embodiments, the oxygen protecting group is an oxidation-reduction sensitive oxygen protecting group, such as a benzyl ether which is removed under catalytic hydrogenation conditions. In some embodiments, the oxygen protecting group is a silyl ether, such as TBDMS, TIPS, or TES, which is removed with nucleophilic fluoride.

In some embodiments, the nitrogen protecting group is a base-labile nitrogen protecting group (i.e., one that is removed under basic conditions), such as 9-fluorenylmethyl carbamate (Fmoc). In some embodiments, the nitrogen protecting group is an acid-labile nitrogen protecting group (i.e., one that is removed under acid conditions), such as triphenylmethyl, tert-butyl, tert-butoxycarbonyl, 2-trimethylsilylethoxycarbonyl (Teoc), or 4-methoxybenzyloxycarbonyl. In some embodiments, the nitrogen protecting group is an oxidation-reduction sensitive nitrogen protecting group, such as a benzyl, which can be removed under catalytic hydrogenation conditions.

A skilled artisan will appreciate that while certain protecting groups can be characterized as "acid-labile" or "base-labile," not all acidic or basic conditions will be equally effective in removing all such labile protecting groups. In an illustrative example, exposure to an acidic pH 4 solution can remove one acid-labile oxygen protecting group, but leave another acid-labile oxygen protecting group intact until it is removed by exposure to a more acidic pH 1 solution.

The terms "amine" and "amino" are art-recognized and refer to both unsubstituted and substituted amines and salts thereof, e.g., a moiety that can be represented by the general formulae:

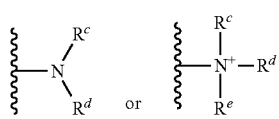

wherein $R^c$, $R^d$, and $R^e$ each independently represent a hydrogen, an alkyl, an alkenyl, —$(CH_2)_m$—$R^f$, or $R^c$ and $R^d$ taken together with the N atom to which they are attached complete a heterocycle having from 4 to 8 atoms in the ring structure; $R^f$ represents an aryl, a cycloalkyl, a cycloalkenyl, a heterocyclyl or a polycyclyl; and m is zero or an integer from 1 to 8. In preferred embodiments, only one of $R^c$ and $R^d$ is a carbonyl, e.g., $R^c$, $R^d$, and the nitrogen together do not form an imide. In even more preferred embodiments, $R^c$ and $R^d$ (and optionally $R^e$) each independently represent a hydrogen, an alkyl, an alkenyl, or —$(CH_2)_m$—$R^f$. In certain embodiments, the amino group is basic, meaning the protonated form has a $pK_a \geq 7.00$.

As used herein, an "organic base" is an organic compound comprising at least one basic amino group. The organic base may comprise an alkyl amine, such as triethylamine, diethylamine, and/or diisopropylethylamine, and/or a cyclic amine, such as morpholine, piperidine, piperazine, pyrrolidine, cyclobutylamine, and/or cycloheptylamine.

As used herein, an alcohol includes an organic compound that is or comprises a hydroxyalkyl group. Exemplary alcohols include methanol, ethanol, isopropanol, n-propanol, n-butanol, sec-butanol, tert-butanol, and n-pentanol. In an illustrative example, an alcohol can comprise, consist essentially of, or consist of methanol.

The term "pharmaceutically acceptable salt" refers to the relatively non-toxic, inorganic and organic acid addition salts of a compound, e.g., a compound of formula (V) or (Vb). These salts can be prepared in situ during the final isolation and purification of the compound, or by separately admixing, e.g., reacting, a purified compound in its free base form with a suitable organic or inorganic acid, and isolating the salt thus formed. Representative salts include the bromide, chloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulfonate salts, and amino acid salts, and the like. See, for example, Berge et al. 1977, "Pharmaceutical Salts," J. Pharm. Sci. 66: 1-19. Acceptable salts also include trifluoroacetate salts.

As used herein, "active ceftolozane" refers to the equivalent amount of ceftolozane zwitterion (i.e., compound (VIb) as described herein) in a preparation of ceftolozane that may be impure and/or comprise a salt, e.g., a sulfate salt. For example, a 100% pure preparation of 1 kg ceftolozane sulfate (i.e., compound (VI) described herein) comprises 0.87 kg active ceftolozane.

A "volume" of solvent is art-recognized, and is meant to refer to 1 L of solvent per 1 kg of compound used. For example, for a 50-kg scale reaction of a compound of formula (III') as described herein, 5 volumes of N-methylpyrrolidone is 250 L.

As described herein, the stated temperature for a process, e.g., a reaction or a separation, refers to the temperature or temperature ranges for a substantial period during the process. In some embodiments, the temperature or temperature range is maintained for about 20%, about 30%, about 40%, about 50%, about 60%, about 70%, about 80%, about 90%, about 95%, about 98%, about 99% or greater than about 99% of the total process time. In some embodiments, the temperature range of the process is within ±10° C., ±5° C., ±3° C., or ±2° C., of the upper and/or lower temperature in the stated range for about 70%, about 80%, about 90%, about 95%, about 98%, about 99%, or greater than about 99% of the total process time. In certain embodiments, the temperature of the process is within ±10° C., ±5° C., ±3° C., or ±2° C., of the stated temperature for about 70%, about 80%, about 90%, about 95%, about 98%, about 99%, or greater than about 99% of the total time for the process.

6.2. General Method of Making a Compound of Formula (Vb')

A general route to make a compound of formula (Vb') is depicted in Scheme 1. A compound of formula (III') can be admixed with a compound of formula (IV') under conditions suitable to provide a compound of formula (V'). Exemplary synthetic methods to make a representative compound of formula (III') and/or compound of formula (IV') are described in U.S. Pat. Nos. 7,192,943 and 7,129,232, as well as Toda et al., "Synthesis and SAR of novel parenteral anti-pseudomonal cephalosporins: Discovery of FR264205," Bioorganic & Medicinal Chemistry Letters, 18, 4849-4852 (2008).

Scheme 1

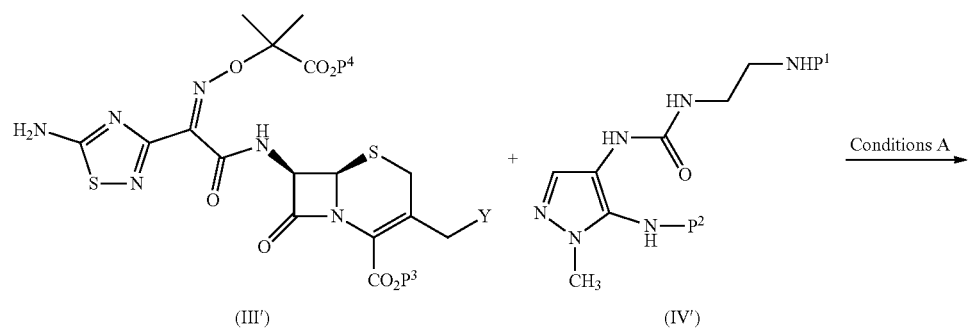

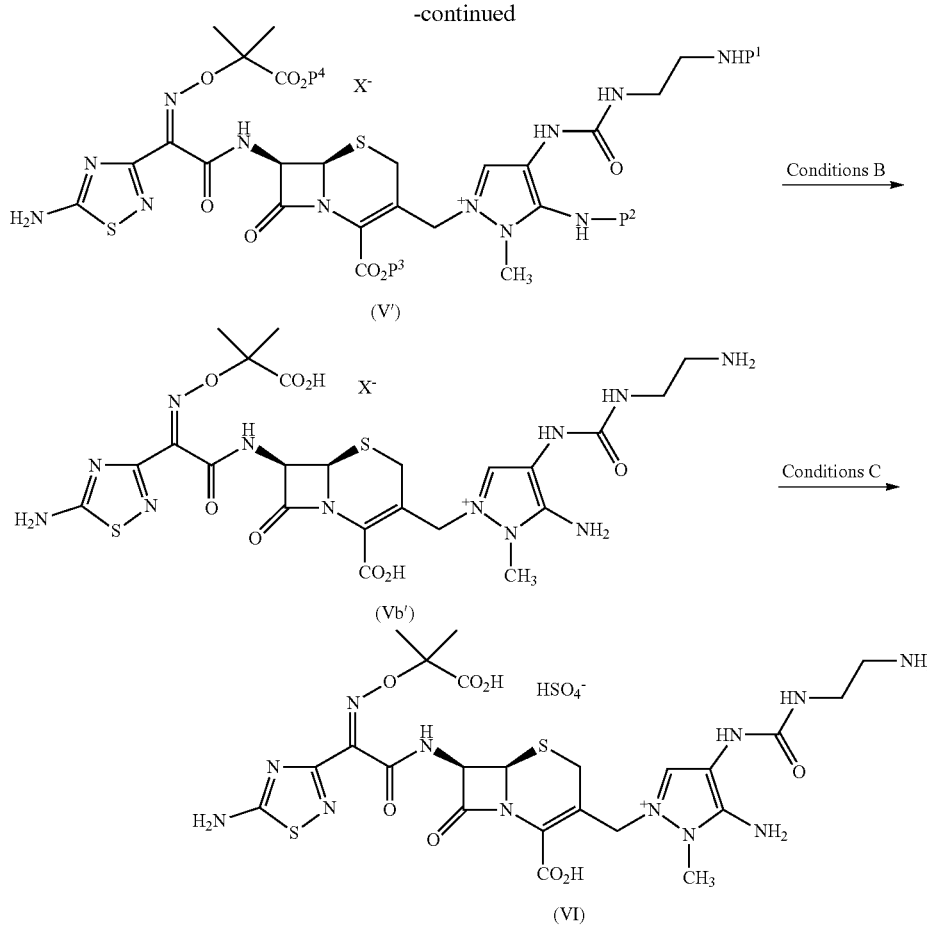

In some embodiments, $P^1$ and $P^2$ are each independently a nitrogen protecting group, such as an acid-labile nitrogen protecting group, for example, tert-butyl, tert-butoxycarbonyl, triphenylmethyl, tetrahydropyranyl, or 2-nitrobenzenesulfenyl. $P^1$ and $P^2$ can be the same or different. In some embodiments, $P^1$ is tert-butoxycarbonyl (i.e., Boc). In some embodiments, $P^2$ is triphenylmethyl (i.e., trityl).

In some embodiments, $P^3$ and $P^4$ are each independently an oxygen protecting group, such as an acid-labile oxygen protecting group, for example, tert-butyl, 4-methoxybenzyl, tetrahydropyranyl, triphenylmethyl, trimethylsilyl, or tert-butyldimethylsilyl. $P^3$ and $P^4$ can be the same or different. In some embodiments, $P^3$ is 4-methoxybenzyl (i.e., para-methoxybenzyl or PMB). In some embodiments, $P^4$ is tert-butyl.

In some embodiments, Y is halogen, such as Cl, Br, or I. In some embodiments, Y is Cl or I. In some embodiments, Y is Cl or Br, such as Cl.

In some embodiments, $X^-$ is a pharmaceutically acceptable salt, such as trifluoroacetate, bromide, chloride, iodide, or methanesulfonate. In some embodiments, $X^-$ is trifluoroacetate.

In one aspect, provided herein is a method of making a compound of formula (V') comprising admixing a compound of formula (III') and a compound of formula (IV'). As shown in Scheme 1, Conditions A comprise suitable reaction conditions for the admixture of a compound of formula (III') and a compound of formula (IV') to provide a compound of formula (V').

Typically, the admixed compounds are dissolved in an appropriate solvent, such as a polar aprotic solvent, for example, comprising dimethylformamide (DMF), dimethylacetamide (DMA), N-methylpyrrolidone (N-methylpyrrolidinone or NMP), N, N'-dimethylimidazolidinone (DMI), or mixtures thereof. In some embodiments, the solvent comprises, consists essentially of, or consists of N-methylpyrrolidinone. The reaction solvent preferably is present in an amount sufficient to allow for an appreciable rate of bimolecular reaction between the compound of formula (III') and the compound of formula (IV') without undesired side-reactions. In some embodiments, the solvent is present in from about 5.0 to about 7.0, such as from about 5.5 to about 6.5 or from about 5.7 to about 6.4, volumes compared to the compound of formula (III').

Optionally, Conditions A comprise additional reagents that can improve reaction characteristics, e.g., shorten reaction time, provide for higher conversion to product, provide for reduced level of impurities, etc. In some embodiments, Conditions A comprise an exogenous salt, such as toluenesulfonate, trifluoroacetate, bromide, iodide, or mixtures thereof. In an illustrative example, potassium iodide is added to the admixture to accelerate the desired reaction and thus shorten the required reaction time. In some embodiments, the exogenous salt is present in from about 1.6 to about 2.8, such as from about 1.6 to about 2.0, from about 1.6 to about 1.9, from about 1.7 to about 1.9, from about 1.7 to about 2.0, or from about 1.75 to about 1.85, molar equivalents compared to the compound of formula (III').

In some embodiments, Conditions A comprise an activator, such as N-trimethylsilylacetamide or 1, 3-bis(trimethylsilyl)urea (BSU), to accelerate the desired reaction. In some embodiments, Conditions A comprise 1, 3-bis(trimethylsilyl)urea. In some embodiments, the activator is present in from about 3.0 to about 4.6, such as from about 3.5 to about 3.7 or from about 3.55 to about 3.65, molar equivalents compared to the compound of formula (III').

The relative amounts of a compound of formula (III') and a compound of formula (IV') admixed under Conditions A are chosen to provide a compound of formula (V') with minimal amounts of side-products or undesired reactions. Typically, the compound of formula (IV') is in a molar equivalent ratio of from about 1.0:1 to about 1.5:1, such as from about 1.0:1 to about 1.3:1 or about 1.15:1 to about 1.25:1, compared to the compound of formula (III'). In some embodiments, the compound of formula (IV') is in a molar equivalent ratio of about 1.1:1, about 1.2:1 or about 1.3:1, compared to the compound of formula (III').

In some embodiments, a compound of formula (III') has the structure of compound (III).

In some embodiments, a compound of formula (IV') has the structure of compound (IV).

In some embodiments, a compound of formula (V') has the structure of compound (V).

The temperature of the admixture under Conditions A allows for the desired bimolecular reaction to proceed with limited production of side-products. In some embodiments, the temperature is from about 20° C. to about 40° C., such as from about 25° C. to about 32° C. or from about 27° C. to about 30° C.

In some embodiments, Conditions A comprise inert gas conditions. Such reaction conditions can be established and maintained, for example, by conducting Conditions A under an inert gas blanket comprising, e.g., nitrogen, helium, argon, krypton, or mixtures thereof, or by purging, i.e., bubbling such inert gas through, the solvent during reaction. In some embodiments, the solvent is purged with inert gas, such as nitrogen. The inert gas purge can occur for the entire reaction period or for a significant portion of the total time in the reaction, e.g., about 20%, about 30%, about 40%, about 50%, about 60%, about 70%, about 80%, about 90%, about 95%, about 97%, about 99%, or greater than about 99% of the total time of the reaction. In some embodiments, the inert gas purge is from about 0.2 m$^3$/h to about 1.2 m$^3$/h, such as from about 0.3 m$^3$/h to about 1.2 m$^3$/h, from about 0.5 m$^3$/h to about 1.2 m$^3$/h, from about 0.7 m$^3$/h to about 1.2 m$^3$/h, from about 0.9 m$^3$/h to about 1.2 m$^3$/h, or from about 1.0 m$^3$/h to about 1.2 m$^3$/h, per kilogram of the compound of formula (III').

In another aspect, provided herein is a method of making a compound of formula (Vb') from a compound of formula (V'). As depicted in Scheme 1, Conditions B are suitable to remove the protecting groups P$^1$, P$^2$, P$^3$, and P$^4$ from the compound of formula (V') to provide the compound of formula (Vb'). In some embodiments, Conditions B comprise an acid of formula HX, wherein HX is trifluoroacetic acid, hydrogen bromide, hydrogen chloride, hydrogen iodide, or methanesulfonic acid. In certain embodiments, HX is trifluoroacetic acid. A skilled artisan will appreciate that a given selection of HX, e.g., trifluoroacetic acid, will provide the corresponding X-salt, e.g., the trifluoroacetate salt, in the compound of formula (V'). In some embodiments, the acid of formula HX is present in from about 4.5 to about 6.0, such as from about 4.5 to about 5.5, from about 4.8 to about 5.4, from about 4.7 to about 5.4, from about 5.0 to about 5.4, from about 4.9 to about 5.3, or from about 4.9 to about 5.4, volumes per kilogram of the compound of formula (V'). As used herein, the volume of acid is calculated using neat anhydrous acid, e.g., trifluoroacetic acid, or concentrated aqueous acid, e.g., 37% hydrochloric acid.

The temperature of the admixture under Conditions B allows for the desired deprotection reaction to proceed with limited production of side-products. In some embodiments, the temperature is from about 15° C. to about 28° C., such as from about 21° C. to about 25° C., from about 17° C. to about 25° C., or from about 18° C. to about 22° C.

In some embodiments, a compound of formula (Vb') has the structure of compound (Vb).

In an aspect, provided herein is a method of making a compound of formula (VI) from a compound of formula (Vb'). As depicted in Scheme 1, Conditions C are suitable to exchange the salt in a compound of formula (Vb') for a sulfate salt to provide compound (VI). In some embodiments, Conditions C comprise contacting a compound of formula (Vb') with sulfuric acid to provide compound (VI).

In some embodiments, Conditions C comprise the purification of a compound of formula (Vb') before contacting the compound with sulfuric acid. In some embodiments, the purification comprises one or more filtrations, e.g., filtration through a resin, nanofiltration, and/or diafiltration.

In some embodiments, the purification comprises filtration through a resin, e.g., a hydrophobic resin, e.g., HP20L (such as Diaion® HP-20). The amount of resin can vary, but typically is in a range of from about 7.5 volumes to about 8.9 volumes, such as from about 7.6 volumes to about 8.6 volumes, from about 7.8 volumes to about 8.5 volumes, from about 8.1 volumes to about 8.5 volumes, compared with a compound of formula (Vb'). The temperature of filtration can affect the efficiency of separation from impurities and yield of the compound of formula (Vb'), and typically is in the range of from about 20° C. to about 30° C., such as from about 22° C. to about 28° C., from about 23° C. to about 27° C., from about 24° C. to about 26° C., or from about 23.5° C. to about 26.5° C. In some embodiments, the eluting solvent comprises an acidic solution, e.g., water with a pH of from about 1.0 to about 2.7, such as from about 1.2 to about 2.0, from about 1.2 to about 1.8, or from about 1.3 to about 1.7.

In some embodiments, the purification comprises nanofiltration, e.g., through a polymeric membrane such as GE-Osmonics (Desal) DL, Dow Filmtec™ NF-270, or Trisep XN45, for example, Trisep XN45. The temperature of filtration can affect the efficiency of separation from impurities and yield of the compound of formula (Vb'), and typically is in the range of from about 0° C. to about 20° C., such as from about 0° C. to about 15° C., from about 2° C. to about 8° C., from about 0° C. to about 8° C., or from about 4° C. to about 10° C. In some embodiments, the solution comprising a compound of formula (Vb') undergoing nanofiltration has a pH of from about 5.5 to about 7.4, such as from about 6.0 to about 7.4, from about 6.2 to about 7.2, or from about 6.4 to about 7.0.

After purification of a compound of formula (Vb'), the compound is contacted with sulfuric acid. The amount of sulfuric acid is sufficient to effect salt exchange, and typically is in the range of from about 1.5 to about 3.0, such as from about 1.8 to about 2.8, from about 2.0 to about 3.0, from about 2.2 to about 3.0, from about 2.2 to about 2.8, or from about 2.3 to about 2.7, molar equivalents compared with the compound of formula (Vb').

6.3. Method of Making Compound (Vb)

Figure 2:
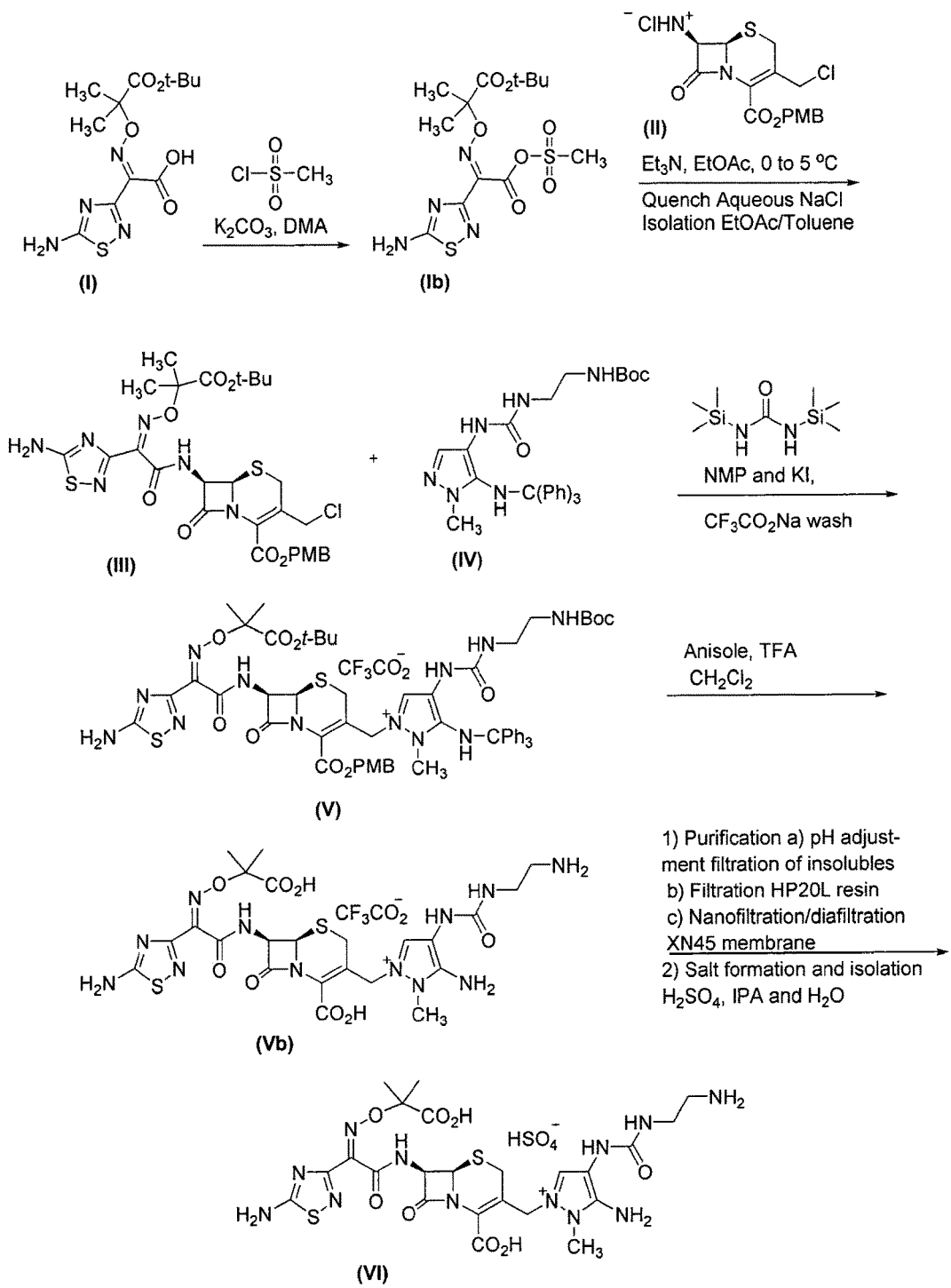
FIG. 2 shows a synthetic scheme to prepare compound (VI) (ceftolozane sulfate) in part using Methods 1 and 2.

Ceftolozane sulfate active drug substance can be obtained by methods described in U.S. Pat. Nos. 7,192,943 and 7,129,232, as well as Toda et al., "Synthesis and SAR of novel parenteral anti-pseudomonal cephalosporins: Discovery of FR264205," Bioorganic & Medicinal Chemistry Letters, 18, 4849-4852 (2008), incorporated herein by reference. Referring to FIG. 2, synthesis of ceftolozane can be performed via activation of the thiadiazolyl-oximinoacetic acid derivative compound (I) with methanesulfonyl chloride and $K_2CO_3$ in DMA at 10° C., followed by coupling with the 7-aminocephem compound (II) by means of $Et_3N$ in cold EtOAc/$H_2O$, affords amide compound (III). Substitution of the allylic chloride of compound (III) with 4-[(N-Boc-aminoethyl)carbamoylamino]-1-methyl-5-tritylaminopyrazole compound (IV) in the presence of 1,3-bis(trimethylsilyl)urea (BSU) and KI in DMF then affords the protected pyrazolium adduct compound (V), which, after deprotection with trifluoroacetic acid in anisole/$CH_2Cl_2$, can be isolated as the hydrogen sulfate salt compound (VI) by treatment with $H_2SO_4$ in isopropanol/$H_2O$.

Figure 3:
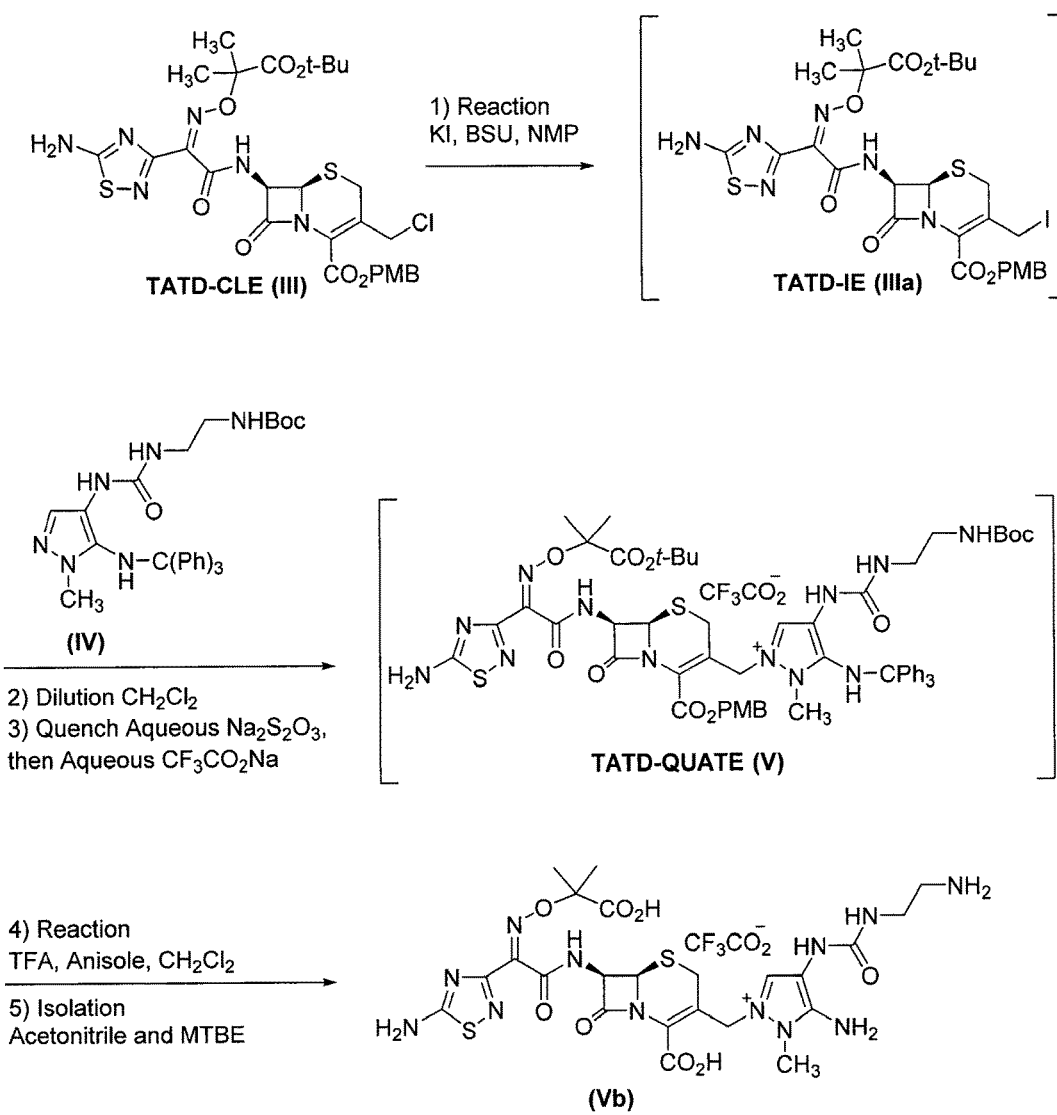
FIG. 3 shows a synthetic scheme to prepare compound (Vb) (ceftolozane TFA crude) using Method 1.
Figure 4:
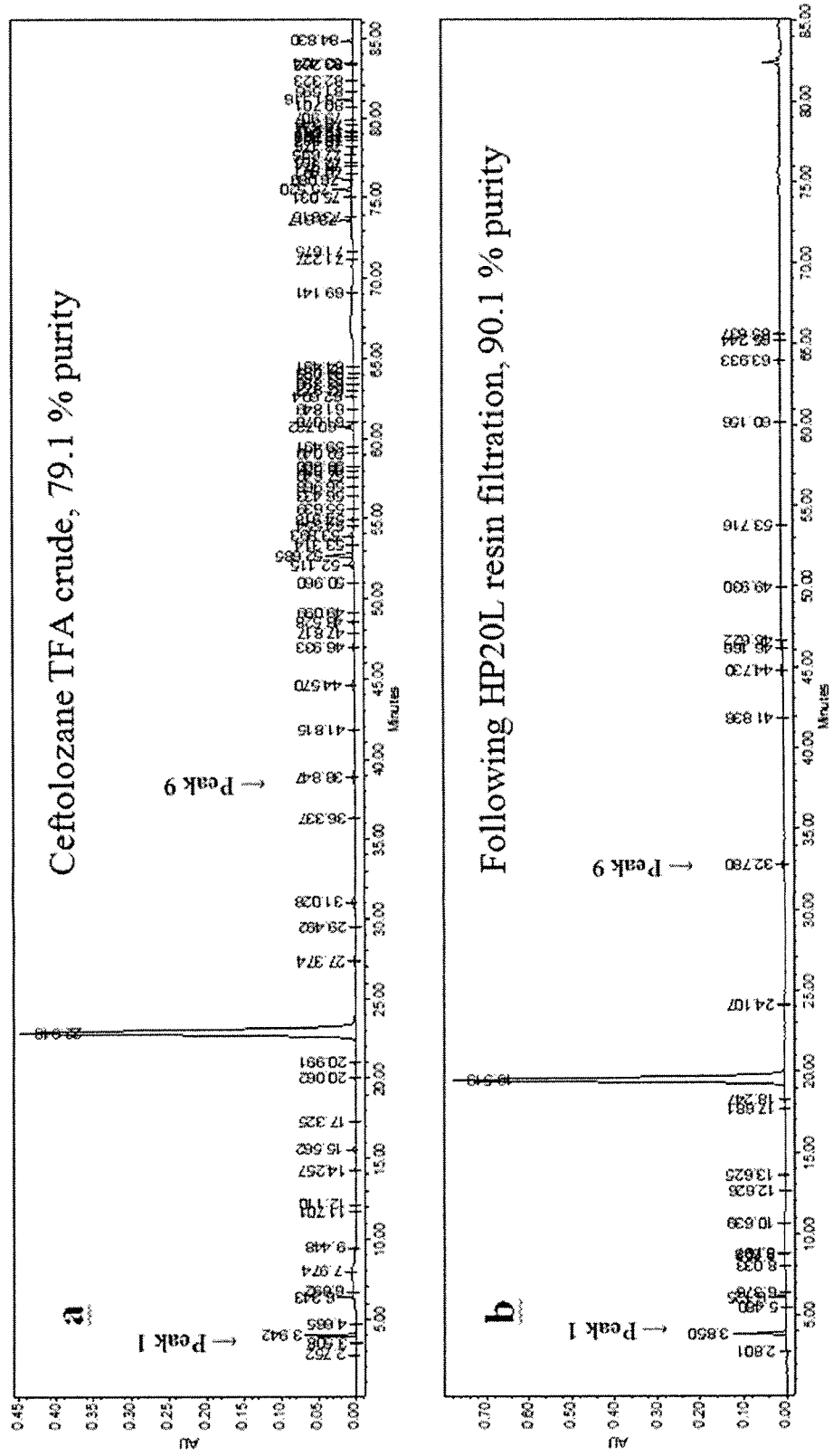
FIG. 4 shows HPLC chromatograms taken after certain steps of Method 2.

The compound (Vb) (ceftolozane TFA crude) of FIG. 3 can be processed to yield compound (VI) (ceftolozane hydrogen sulfate salt or ceftolozane sulfate), as depicted in FIGS. 4 and 5. Accordingly, there is a need for methods of, and improved processes for, reproducibly preparing high quality and high purity compound (VI). The methods and processes may also be important for synthesis of ceftolozane sulfate on a commercial scale with volumetric efficiency and reduced cycle times. Furthermore, the improved process provides safer and more facile manufacturing procedures, higher throughput and a lower solvent and aqueous waste burden because of the higher volumetric efficiency of the process. There is also a need for chemical intermediates useful in such methods.

As shown in FIG. 2, compound (III) can prepared by activating compound (I) with methanesulfonyl chloride (MsCl) and reacting the resulting mixed anhydride with compound (II). Compound (IV) can be prepared according to the method shown in FIG. 1 (See, e.g., Bioorganic & Medicinal Chemistry Letters, 18, 4849-4852 (2008)). Compound (V) (ceftolozane TFA, crude) is prepared by activating compound (III) with potassium iodide and reacting the resulting allylic iodide with compound (IV), followed by global deprotection with trifluoroacetic acid. Compound (VI) (ceftolozane sulfate) is prepared using a process comprising purifying ceftolozane (compound (Vb)) via pH adjustment, removal of insoluble material, then passage through a resin, followed by salt formation with sulfuric acid and isolation from aqueous isopropanol.

In an aspect, provided herein is a method for making a compound (V):

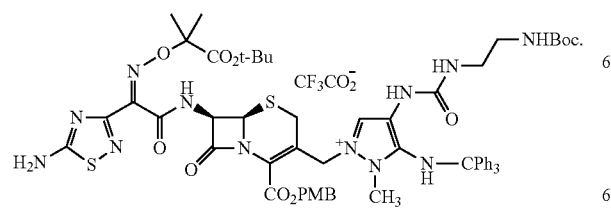

(V)

In some embodiments, the method for making compound (V) comprises use of compound (III):

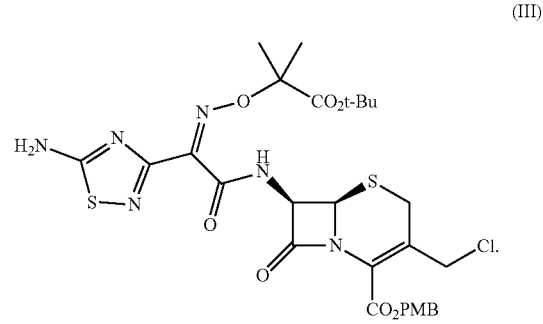

(III)

In an embodiment of the methods described herein, compound (IIIa), also referred to herein as TATD-IE, is formed.

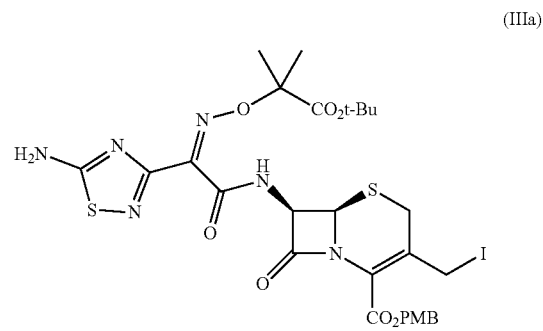

(IIIa)

In some embodiments, the method for making compound (V) also comprises use of compound (IV):

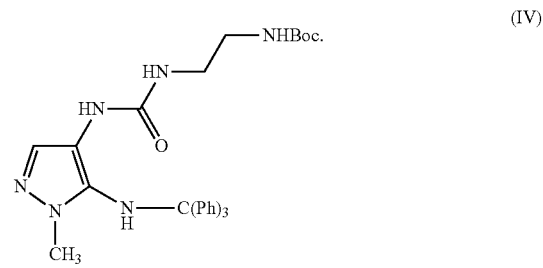

(IV)

In an embodiment, the method comprises the step of forming compound (V) (See, e.g., FIG. 3 and Example 1) by admixing, e.g., reacting, compound (III) with compound (IV) under reaction conditions to provide, e.g., to form, compound (V). It was observed that use of between about 1.15 and 1.25 equivalents of compound (IV) to 1.0 equivalent of compound (III) at a reaction temperature of between about 27 and 30° C. resulted in increased product quality and a desirable reaction rate to yield compound (V) (TATD-QUATE). In an embodiment, the method comprises between about 1.15 and 1.23 equivalents of compound (IV) to compound (III). In a preferred embodiment, the method comprises about 1.2 equivalents of compound (IV) to compound (III). In another embodiment, the method is carried out at a temperature between about 27 and 30° C.

In another embodiment, the method further comprises the step of washing the reaction mixture with aqueous $CF_3CO_2Na$ (resulting in the $CF_3CO_2^-$ salt, compound (V)).

In an embodiment, the methods described herein further comprise providing, e.g., forming compound (Vb), also referred to herein as ceftolozane TFA.

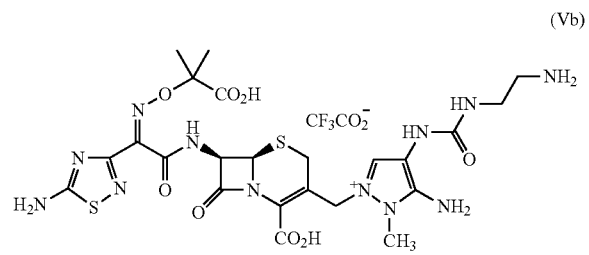

(Vb)

The organic layer comprising compound (V) (TATD-QUATE) can be used directly in the deprotection reaction to obtain compound (Vb) (see, e.g., steps B and C of Example 1). The deprotection comprises reaction of compound (V) with TFA (trifluoroacetic acid). In the deprotection reaction, a reaction temperature of 18-22° C. can be used. Formation of compounds of interest, e.g., compound (V) and compound (Vb), were detectable and analyzed by the HPLC method of Example 4.

In another aspect, provided herein is a method for making compound (VI), also referred to herein as ceftolozane sulfate.

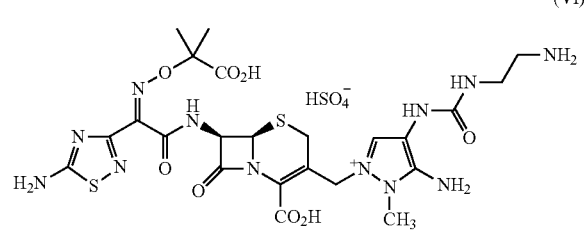

(VI)

Formula (VI) can be prepared using a method or a process comprising the steps of:

(a) forming a solution comprising compound (Vb):

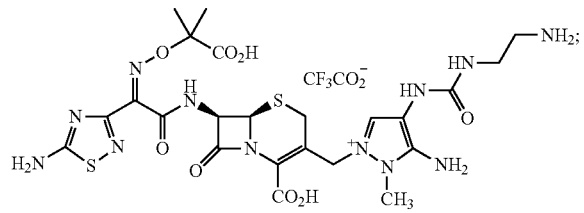

(Vb)

(b) adjusting the final pH of the solution to between 1.2 and 2.0 and removing insoluble material;

(c) filtering the resulting solution of step (b) through a resin; and (d) adding sulfuric acid to obtain compound (VI):

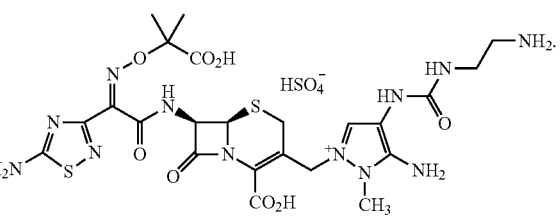

(VI)

In some embodiments, compound (VI) can be prepared by contacting compound (Vb) with sulfuric acid.

In some embodiments, step (b) comprises the steps of:

(i) adding ammonium hydroxide until the pH of the solution is between 6.0 and 7.0; and (ii) adding hydrochloric acid until the pH of the solution is between 1.2 and 2.0.

In another embodiment, the removal of the insoluble material in step (b) is achieved by centrifugation.

In an embodiment, the resin of step (c) is a hydrophobic resin. In a further embodiment, the resin of step (c) is HP20L resin, e.g., Diaion® HP-20. In another embodiment, the solution filtered through the resin in step (c) has a pH between about 1.2 and 2.0.

In some embodiments, the method comprises formation of compound (VIb), the zwitterionic form of ceftolozane ("active ceftolozane") having the following structural formula:

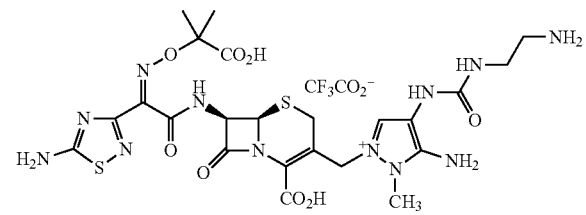

(VIb)

Referring to FIGS. 4 and 5 and Example 3, method 2 comprises the purification of compound (Vb) (ceftolozane TFA crude) and formation of compound (VI) (ceftolozane sulfate). A low pH range of the solution comprising compound (Vb) was deemed critical to remove insoluble impurities and late-eluting impurities by filtration.

One aspect of the invention involves a method or a process of making compound (Vb):

comprising the following steps:
(a) admixing, e.g., reacting, a compound (III):

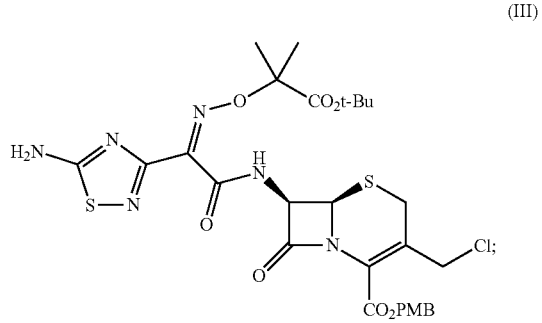

with compound (IV):

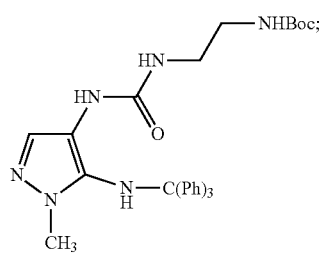

under reaction conditions to provide, e.g., form compound (V):

In some embodiments, the deprotecting comprises contacting compound (V) with trifluoroacetic acid.

In some embodiments, reaction completion, or the maximum formation of compound (V), was determined by measuring the remaining amount of compound (IIIa). For example, the reaction can be considered complete when less than about 5.0% of compound (IIIa):

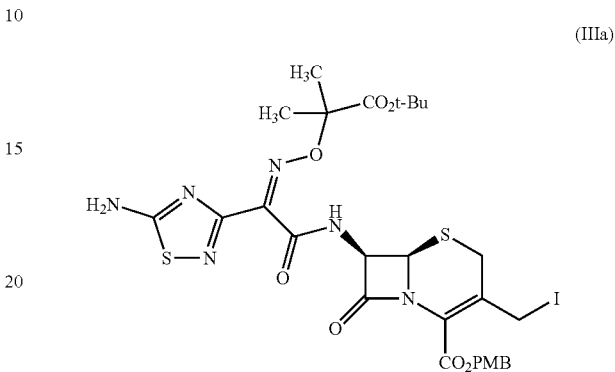

remains as measured by high performance liquid chromatography (HPLC) (e.g., by the HPLC method provided in Example 4) with respect to compound (V).

7. EXAMPLES

Example 1: Method of Preparation of Compound (Vb) (Ceftolozane TFA Crude)

Preparation of ceftolozane TFA crude comprises the following steps (summarized in FIG. 2):

(A) Conversion of TATD-CLE to TATD-IE and in situ coupling with UBT to form the non-isolated intermediate TATD-QUATE;

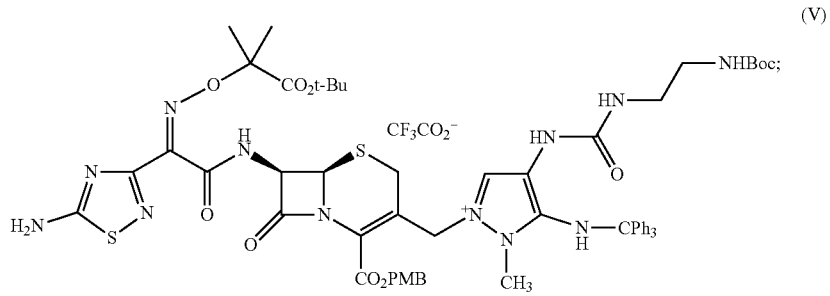

and
(b) deprotecting compound (V) under conditions to form compound (Vb), wherein the ratio of compound (III) to compound (IV) in step (a) is about 1:1.2.

(B) Dilution and quench of TATD-QUATE reaction mixture;
(C) Deprotection of TATD-QUATE to yield ceftolozane TFA crude; and
(D) Isolation of ceftolozane TFA crude.

(A) Formation of Compound (V) (TATD-QUATE) via Compound (IIIa) (TATD-IE)

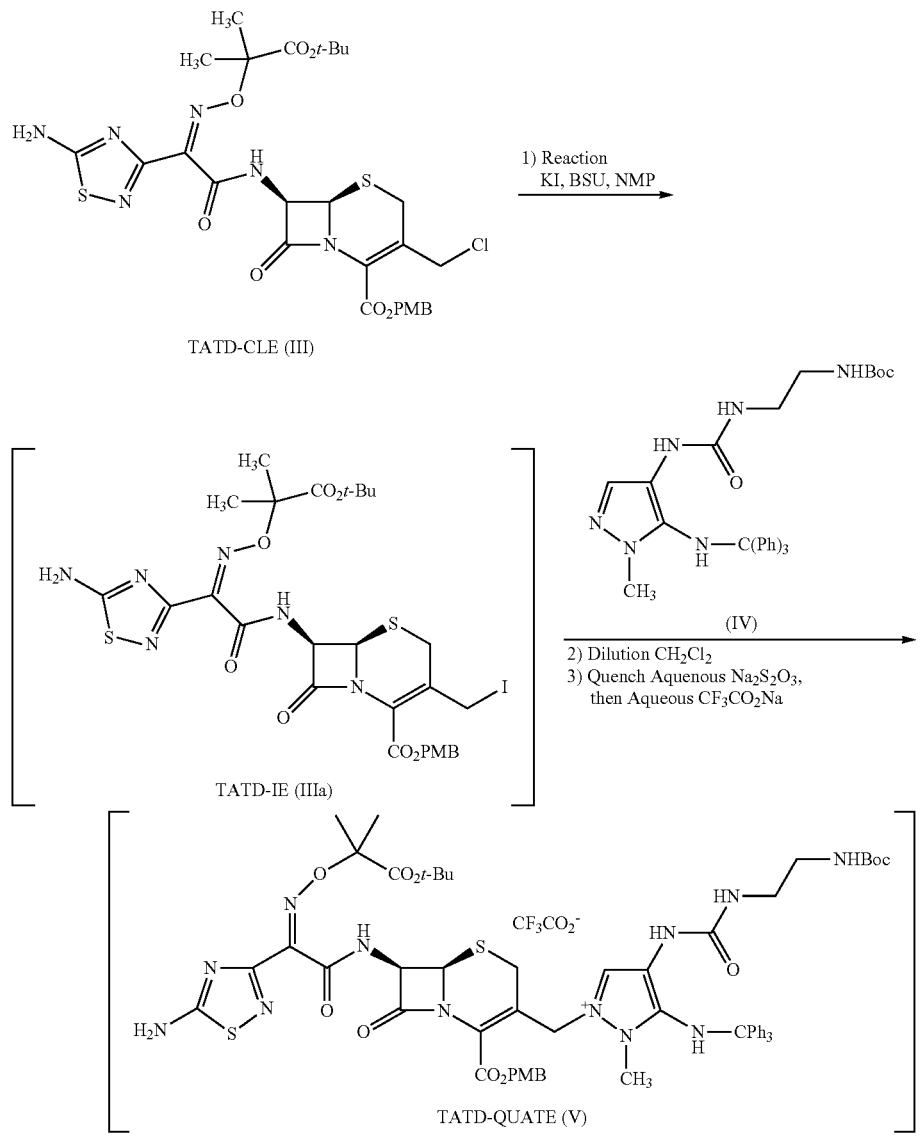

A reactor, or reactor 1, was charged with N-methylpyrrolidone (i.e., N-methylpyrrolidinone or NMP, 287.8 g, 280 mL, 5.6 volumes) at a temperature between 15 and 25° C. Then reactor 1 was charged with compound (IV) (UBT, 47.62 g, 88.08 mmol, 1.2 equiv), and the batch temperature was adjusted to about 29° C., which was maintained until the completion of the reaction. The reaction was maintained under a nitrogen atmosphere. Reactor 1 was charged with 1,3-bis(trimethylsilyl)urea (BSU, 13.50 g, 66.06 mmol, 0.9 equiv), and the batch was stirred for 30 min. Reactor 1 was charged with compound (III) (TATD-CLE, 53.02 g, 50.0 g active, 73.40 mmol, 1.0 equiv), and the reactor walls were washed with NMP (20.6 g, 20 mL, 0.4 volumes). The batch in reactor 1 was stirred for 30 to 60 minutes. Then the batch was charged with potassium iodide (KI, 21.93 g, 132.12 mmol, 1.8 equiv). After addition of potassium iodide, reactor 1 was charged with 1,3-bis(trimethylsilyl)urea (BSU, 40.5 g, 198 mmol, 2.7 equiv) and stirred. The reaction was deemed complete when <5.0% of compound (IIIa) (TATD-IE) remained compared with compound (V) (TATD-QUATE) as determined by HPLC using the method of Example 4.

(i) Preferred Equivalents of Compound (IV) (UBT) and Temperature

In this coupling, compound (IV) (UBT) equivalents were deemed critical because undercharging compound (IV) (UBT) would result in reduction of the rate of reaction, and overcharging compound (IV) (UBT) would result in an increased amount of residual compound (IV) (UBT); both outcomes would lead to lower quality product (Table 1). Additionally, a sustained temperature excursion above the normal operating range will result in a decrease in both the purity and yield of compound (V) (TATD-QUATE). Conversely, a sustained excursion below the normal operating range resulted in a reduced reaction rate, allowing degradation to occur.

TABLE 1

Data on Reagent Parameters

| Process parameter | Type | Normal Operating Range |
|---|---|---|
| Potassium iodide (equiv) | Key | 1.75-1.85 |
| UBT (equiv) | Critical | 1.15-1.25 |
| N-methylpyrrolidone (vol) | Key | 5.7-6.4 |
| 1,3-Bis(trimethylsilyl)urea (BSU) (equiv) | Key | 3.55-3.65 |
| Reaction temperature (° C.) | Critical | 27-30 |

(ii) Impact on Subsurface Nitrogen Purge

Three process parameters were evaluated for statistical significance during the coupling reaction of compound (III) with compound (IV) on the yield and purity of compound (V): nitrogen flow, reactor capacity, and agitation (Tables 2-4). Nitrogen flow had a statistically significant effect on the yield and purity, while both agitation rate and reactor capacity had no significant effects (Table 2).

TABLE 2

Effect of Non-Reagent Process Parameters on Compound (V)

| Process parameter | Yield* | Purity* |
|---|---|---|
| Nitrogen flow ($m^3/h \cdot kg$) | Significant | Significant |
| Reactor capacity (%) | Not significant | Not significant |
| Agitation (rpm) | Not significant | Not significant |

*Determination of significance was performed using standard Pareto analysis with $\alpha = 0.05$.

Table 3 depicts the results of two exemplary trials (Trial 1 and Trial 2) illustrating the difference between a preparation of compound (V) performed with an above surface nitrogen blanket vs. one performed with a subsurface nitrogen purge of the solvent throughout the reaction. In both trials, 150 kg of compound (III) was used as starting material. Trial 1 was performed with an above surface nitrogen blanket only, while Trial 2 had a 150-180 $m^3/h$ subsurface nitrogen purge of the solvent. Trial 2 with the subsurface nitrogen purge showed a higher amount of isolated product (196 kg vs. 173 kg), greater potency (42.6% vs. 40.4%), greater purity of product (78.4% vs. 74.9%), and a higher molar yield (57% vs. 48%) when compared with Trial 1.

TABLE 3

Results of Above Surface and Subsurface Nitrogen Purge Trials

| | Trial | |
|---|---|---|
| | 1 | 2 |
| Starting amount compound (III) | 150 kg | 150 kg |
| Nitrogen supply | Above surface blanket | 150-180 $m^3/h$ subsurface purge |
| Product amount | 173 kg | 196 kg |
| Potency | 40.4% | 42.6% |
| Purity | 74.9% | 78.4% |
| Molar yield | 48% | 57% |

In the coupling reaction, inadequate subsurface nitrogen flow rate results in an increased level of impurities, leading to lower quality product. As shown in Table 4, the normal operating range for the subsurface nitrogen purge during the coupling reaction is from about 0.3 $m^3/h \cdot kg$ to about 1.2 $m^3/h \cdot kg$.

TABLE 4

Normal Operating Parameters for Significant Variable

| Process parameter | Type | Normal Operating Range |
|---|---|---|
| Nitrogen purge ($m^3/h \cdot kg$) | Critical | 0.3-1.2 $m^3/h \cdot kg$ |

Without intending to be limited by theory, the subsurface purge of nitrogen gas (i.e., bubbling nitrogen gas through the solvent during the entire reaction) is believed to remove the reaction mixture of volatile reactive side-products, such as chlorotrimethylsilane or iodotrimethylsilane, that can be produced under conditions of the reaction, and that can lead to undesirable side reactions. It is expected that other inert gases, such as helium, argon, or krypton, can serve the purpose of nitrogen gas as exemplified herein.

(B) Dilution, Quench, and Isolation to Obtain Compound (V) (TATD-QUATE)

The batch in reactor 1 was cooled to a temperature between 10 and 15° C. and charged with $CH_2Cl_2$ (dichloromethane, 465.5 g, 350 mL, 7.0 volumes). Then the batch was cooled to a temperature between −10 and 5° C. The batch in reactor 1 was charged with 4.4% (w/v) sodium chloride (NaCl) at pH 4 to 6 (300 mL), and the batch was stirred for 25 to 35 minutes, while maintaining the batch temperature between 0 and 5° C. Stirring was discontinued and the phases were allowed to separate for 20 to 40 minutes. The lower organic layer was collected and transferred to reactor 2. The remaining aqueous layer in reactor 1 was extracted with $CH_2Cl_2$ a second time and the resulting organic layer was combined with the first organic layer. A chilled aqueous solution of 10% (w/v) NaCl and 5% (w/v) $Na_2S_2O_3 \cdot 5H_2O$ (300 mL; temperature between 0 to 5° C.) was added to reactor 2, and was stirred for 25 to 35 minutes. Then, stirring was discontinued and the phases were allowed to separate for 20 to 40 minutes. The $CH_2Cl_2$ layer was separated from the aqueous layer, and the organic layer was transferred to reactor 1.

An aqueous solution of 15% (w/v) $CF_3CO_2Na$ (sodium trifluoroacetate or NaTFA) was prepared by adding $CF_3CO_2Na$ (112.5 g) to water (750 mL, 15 volumes) at ambient temperature. Then the solution was cooled to a temperature between 12 and 18° C., and the pH of the solution was adjusted to a value between 2.9 and 3.1 via the addition of $CF_3CO_2H$ (trifluoroacetic acid or TFA), while maintaining a temperature of the solution between 12 and 18° C. Once the desired pH was reached, the solution was cooled to a temperature between 0 and 5° C. The organic phase solution of reactor 1 was washed three times with the aforementioned aqueous $CF_3CO_2Na$ solution, using one third of the solution (about 250 mL, 5.0 volumes) for each wash. The resulting biphasic mixture was agitated for 25 to 35 minutes, then the phases were allowed to separate for 20 to 40 minutes. The dark lower organic phase was collected in-between each wash. The solution yield of compound (V) (TATD-QUATE) was determined to be 65% based on HPLC analysis (using, e.g., the HPLC method of Example 4) relative to a standard concentration.

TABLE 5

Analysis of Process Parameters for the Purification of Compound (V)

| Process parameter | Yield* | Purity* |
|---|---|---|
| Dichloromethane (vol) | Not significant | Not significant |
| pH of the first NaCl wash | Not significant | Significant |

TABLE 5-continued

Analysis of Process Parameters for the Purification of Compound (V)

| Process parameter | Yield* | Purity* |
|---|---|---|
| Temperature of operation (° C.) | Not significant | Not significant |
| Sodium trifluoroacetate (w/v %) | Not significant | Not significant |

*Determination of significance was performed using standard Pareto analysis with α = 0.05.

TABLE 6

Normal Operating Parameters for Statistically Significant Variable

| Process parameter | Type | Normal Operating Range |
|---|---|---|
| pH of the first NaCl wash | Key | 4-6 |

Four process parameters in the aqueous wash purification of compound (V) were evaluated for statistical significance on the yield and purity of isolated compound (V) (Tables 5 and 6). The results indicated that pH of the NaCl wash had a statistically significant effect on the purity, while none of the parameters were significant for yield. As shown in Table 6, the normal operating range for the pH of the NaCl wash is from about 4 to about 6, but should be no less than about 1.5. The pH of the solution can be adjusted with aqueous HCl or aqueous NaOH as necessary to be within the acceptable range.

(C) Deprotection of TATD-QUATE (V) and Isolation of Ceftolozane TFA Crude (Vb)

by vacuum distillation to 2 volumes (100 mL), while maintaining the batch temperature at 10° C. Subsequently, the batch was cooled to 3° C., and reactor 2 was charged with anisole (34.8 g, 35 mL, 0.7 volumes), while maintaining the batch temperature at 3° C. Then reactor 2 was charged with $CF_3CO_2H$ (TFA, 372.2 g, 250 mL, 5.0 volumes) via slow addition over 30 minutes (at a rate of about 8.3 mL/min), while maintaining the batch at a temperature below 20° C. The batch was stirred at 20° C. for 4 to 8 hours. A sample of the reaction mixture was analyzed by the HPLC method of Example 1, and the reaction was deemed complete when ≤2.0% of compound (V) remained relative to ceftolozane. The reaction was complete after about 6 hours.

Reactor 1 was charged with $CH_2Cl_2$ (dichloromethane, 798 g, 600 mL, 12 volumes), and the contents were cooled to −35° C. Then, the batch from reactor 2 was added to the cold $CH_2Cl_2$ in reactor 1. Then the contents of reactor 1 were stirred 30 to 40 minutes at −35° C. The phases were allowed to separate and the product-rich lower phase was collected from reactor 1 and transferred to reactor 2. Several separations may be needed to recover the entire product-rich layer.

Reactor 2 was then charged with $CH_3CN$ (acetonitrile or ACN, 59.0 g, 75 mL, 1.5 volumes), and the batch was warmed to 15° C. Then methyl t-butyl ether (MTBE, 370.2 g, 500 mL, 10 volumes) was added to reactor 2 over the course of 30 to 60 minutes (at a rate of 5-10 vol/h), while maintaining the batch temperature at 15° C. The resulting slurry in reactor 2 was stirred for 2 to 4 hours at 15° C. Then the slurry was filtered to afford a solid wet cake, and the cake

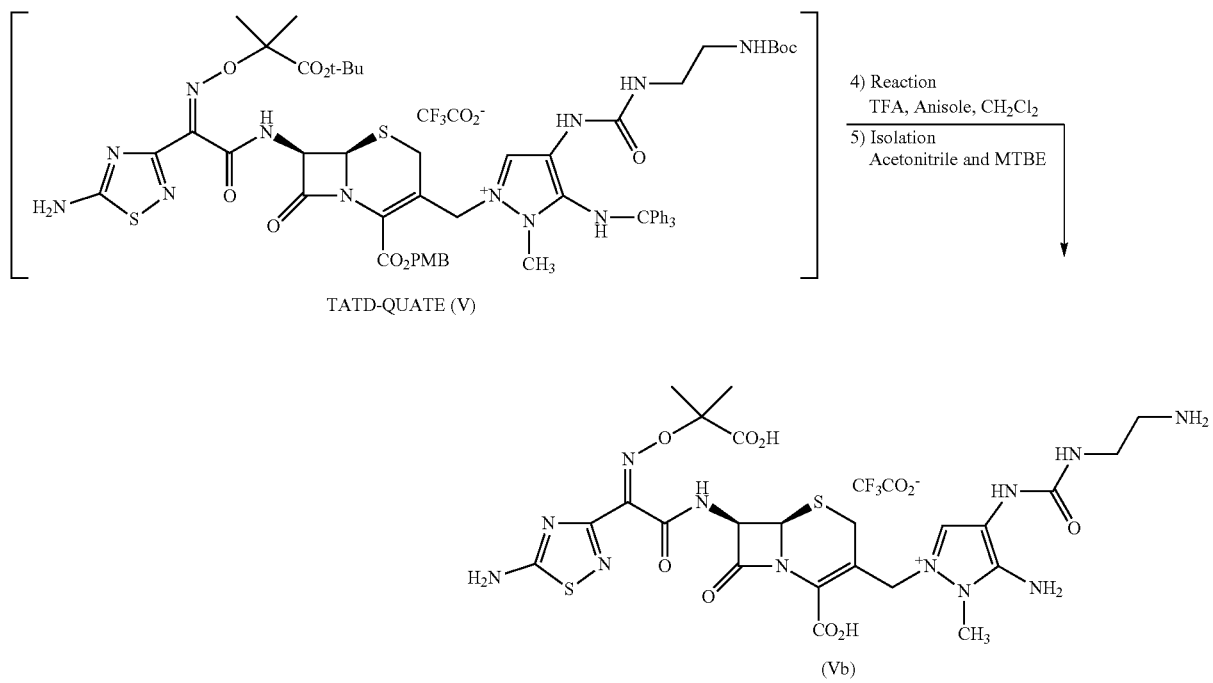

TATD-QUATE (V)

(Vb)

The volume of the solution in reactor 2 was reduced by vacuum distillation to 4.0 volumes (200 mL), while maintaining the batch temperature at 10° C. during distillation. Then reactor 2 was charged with $CH_2Cl_2$ (dichloromethane, 332.5 g, 250 mL, 5.0 volumes), and the volume was reduced was washed twice with MTBE (92.6 g, 125 mL, 2.5 volumes). The solid wet cake was dried under vacuum with a nitrogen flow for at least 8 hours at a temperature less than or equal to 25° C. Compound (Vb) (ceftolozane TFA crude) was isolated as a light yellow to orange solid. Yield: 68.5 g (63%), with an overall purity of 78.2% AUC, as measured by the HPLC method of Example 4.

The overall yield for the Method 1 process run reported above was 68.5 g (63% of theoretical), isolated as a light yellow to orange solid. The overall purity was 78.2% AUC, with a weight assay of 45.0%.

Six process parameters were evaluated for statistical significance for the preparation of compound (Vb) (Table 7). The responses for the study were yield and purity of compound (Vb). The results indicated that anisole charge, trifluoroacetic acid charge and reaction temperature had a statistically significant effect on both the purity and yield of compound (Vb), while the volume of dichloromethane, water content, and N-methylpyrrolidone content had no significant effects on either response.

TABLE 7

Significance of Process Parameters to Make Compound (Vb)

| Process parameter | Yield* | Purity* |
|---|---|---|
| Dichloromethane (vol) | Not significant | Not significant |
| Anisole (vol) | Significant | Significant |
| Trifluoroacetic acid (vol) | Significant | Significant |
| Reaction temperature (° C.) | Significant | Significant |
| Water content of reaction (w/w %) | Not significant | Not significant |
| N-methylpyrrolidone content of reaction (w/w %) | Not significant | Not significant |

*Determination of significance was performed using standard Pareto analysis with $\alpha = 0.05$.

Table 8 provides the proven acceptable range (PAR) and normal operating range (NOR) determined from the studies for selected process parameters along with the type. In this reaction from compound (V) to compound (Vb), a sustained temperature excursion significantly above the normal operating range results in a decrease in both the purity and yield of compound (Vb). Conversely, a sustained excursion significantly below the normal operating range results in a reduced reaction rate, failure to meet IPC and additional degradation of product. The PAR values show acceptable ranges for making compound (Vb) without significant loss of yield and/or purity.

TABLE 8

Statistically Significant Process Parameters to Make Compound (Vb)

| Process parameter | Type | PAR | NOR |
|---|---|---|---|
| Batch volume after final distillation | Key | 1.5-3.0 | 1.8-2.8 |
| Anisole (vol) | Non-critical | 0.1-1.3 | 0.5-0.9 |
| Trifluoroacetic acid (vol) | Key | 4.5-6.0 | 4.9-5.4 |
| Reaction temperature (° C.) | Critical | 17-25 | 18-22 |
| Separation temperature (° C.)* | Key | −40 to −25 | −40 to −30 |

*Refers to the temperature during separation of lower product-rich layer from the upper dichloromethane layer Example 2: Reaction Parameters for the Formation of TATD-QUATE Table 9 summarizes the preferred parameters used for the formation of TATD-QUATE. As shown in Table 9, the proven acceptable range (PAR) for UBT is from about 1.0 to about 1.3 equivalents compared with the amount of compound (III). As described above in Table 1, the normal operating range (NOR) for UBT is from about 1.15 to about 1.25 equivalents. As would be expected, the NOR represents more specific embodiments of the PAR for each parameter. Similarly, the NOR for BSU is from about 3.55 to about 3.65 equivalents (Table 1) while the PAR is from about 3.0 to about 4.6 equivalents (Table 9).

TABLE 9

Preferred Reaction parameters used in the formation of TATD-QUATE.

| Process Parameter | Proven Acceptable Range | Criticality Assessment | Justification of Criticality Assessment |
|---|---|---|---|
| Formula (IV) UBT (equiv) | 1.0 to 1.3 | Critical | Above PAR: excess UBT leads to elevated levels of Peak 1 impurity in drug substance. |
| | | | Below PAR: increased level of unreacted TATD-IE due to significantly reduced reaction rate, resulting in elevated levels of impurities Peak 4, Peak 10, and TATD-OH. |
| BSU (equiv) | 3.0 to 4.6 | Key | Above PAR: potential foaming affects productivity. |
| | | | Below PAR: slower conversion to TATD-IE and lower yield. |
| | | | No impact to product purity. |

Example 3: Preparation of Compound (VI) (Ceftolozane Sulfate)

The manufacturing process obtaining ceftolozane sulfate comprises the following steps (see, e.g., FIG. 4):
 pH adjustment to remove insoluble impurities;
 Filtration through a hydrophobic resin (e.g., HP20L resin); and
 Salt formation and isolation.

15% hydrochloric acid; 1749 L, 25 vol) at a pH of 1.2 to 2.0 (target pH of 1.5). The ceftolozane solution (1749 L) in reactor 2 was passed through a heat exchanger to achieve a temperature between 20 and 30° C. (e.g., about 24-26 degrees C., including 23.5-26.5 degrees C.), and then through the HP20L resin. The column was washed with acidic water (acidified with 15% HCl) at a pH of 1.2 to 2.0. The preferred pH is 1.5).

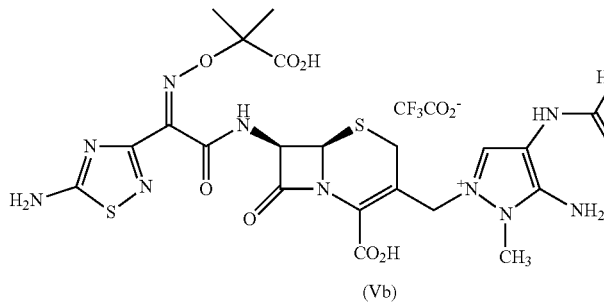

(Vb)

1) Purification comprising
 a) pH adjustment filtration of insolubles
 b) Filtration through resin
2) Salt formation and isolation $H_2SO_4$, IPA and $H_2O$

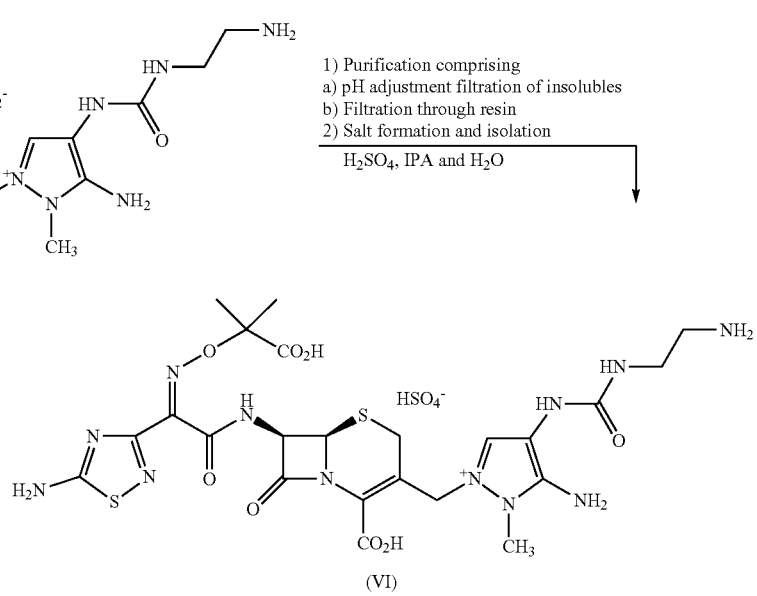

(VI)

(A) pH Adjustment and Filtration of Insoluble Impurities

Reactor 1 was charged with water (1400 kg, 1400 L, 20 volumes), and the water was cooled to a temperature between 3 and 11° C. (preferred temperature of 7° C.). Then reactor 1 was charged with compound (Vb) (ceftolozane TFA crude, 70 kg active ceftolozane, 159.45 kg, 104.995 mol, 1 equiv) in one portion, and the batch was stirred for 30 minutes. A 15% ammonium hydroxide (41 kg, 44 L) solution was charged to reactor 1 until the pH of the solution was between 6.0 and 7.0 (target pH of 6.5). Then the batch was stirred for 15 to 30 minutes (target time of 20 minutes). Then reactor 1 was charged with 15% hydrochloric acid (63 kg, 59 L) until the pH of solution was between 1.2 and 2.0 (preferred pH of 1.5). The batch was stirred for at least 20 min. Perlite (12 kg, 17% by weight of compound (VIb) or active ceftolozane) was charged to reactor 1, and the batch was centrifuged (or filtered) using a filter bag. The solid material in the centrifuge (or filter) was washed with water (560 L, 8 volumes). The solid material in the centrifuge (or filter) was washed a second time with water (280 L, 4 volumes). The filtrates were combined.

The preferred pH range for this step is a pH of 1.2 to 2.0. When the pH is higher than this, impaired performance of the filtration through the hydrophobic resin (e.g., HP20L) can result, and can lead to elevated levels of late-eluting impurities.

(B) Filtration through HP20L Resin

Column 1 was charged with HP20L resin (581 L, 8.3 L/kg active ceftolozane) followed by acidic water (acidified with The load and the wash solutions were collected, and the collections were maintained at a temperature between 0 and 8° C. and a pH between 6.4 and 7.0 via addition of 5% ammonium hydroxide.

The pH range of the acidic wash is critical; with preferred pH levels of between about 1.2 and 2.0. At pH levels higher than this, premature release of the non-polar impurities were captured by the HP20L resin, leading to an increase in late-eluting impurities. In this step, the majority of the non-polar impurities are removed. The efficiency of adsorption of non-polar species to the HP20L resin is controlled by maintaining pH within 1.0-2.7. Because most of the impurities removed in this sub-stage elute after Peak 9, they are collectively referred to as post-Peak 9 impurities. As shown in FIG. 4, the purity of the eluted ceftolozane TFA (i.e., compound (Vb)) solution increased from 79.1 to 90.1%. FIG. 5 depicts the results of HP20L resin purification for multi-kilogram preparations of compound (Vb) from 50 kg to 170 kg. In each batch, the purity is increased from a range of about 75-80% to about 92-95%. Additionally, the post-peak 9 impurities are significantly decreased from a range of about 12-17% to about 0.13-0.33%.

(C) Nanofiltration and Diafiltration

The ceftolozane solution (after filtration through the HP20L resin) was nanofiltered using a Trisep XN45 membrane (Trisep Corporation, Goleta, Calif., USA), while maintaining the temperature between 0 and 8° C. and a pH between 6.4 and 7.0. The temperature and pH were maintained through the nanofiltration step.

Trisep XN45 membrane is a piperazine-based polymeric nanofiltration membrane with a molecular weight cut-off at about 500-700 Daltons. Its nominal solute rejection is about 10-30% NaCl and greater than about 90% for $MgSO_4$ and sucrose.

Subsequently, the ceftolozane solution was diafiltered with water at a constant ceftolozane concentration (35 to 45 g/L). The batch was concentrated by nanofiltration and the solution was collected. Then the nanofiltration system was washed with water and the washes were combined with the rest of the batch.

(D) Salt Formation with $H_2SO_4$ and Isolation

The ceftolozane solution (80 g/L, 690 L) from step C of this example was filtered through a Polish filter (1 μm or another appropriate size) into reactor 4 (glass lined), and the temperature of the batch was adjusted to a temperature between 8 and 12° C.

Reactor 4 was charged with 50% (w/w) sulfuric acid (41 kg, 29 L, 2.5 equiv) over the course of 10 to 30 minutes. Then reactor 4 was charged with a compound (VI) (ceftolozane sulfate seed, 210 g, 0.3% by weight), and the solution was stirred. Then the batch was charged with isopropanol (IPA, 1650 L, 30 volumes) and stirred for 1 to 6 hours.

The contents of reactor 4 were filtered to afford the product as a wet cake. The wet cake was washed with a solution of 4:1 IPA/water. The solid was dried under vacuum using a dry nitrogen purge, with a temperature between 15 and 35° C. Compound (VI) (ceftolozane sulfate) was isolated as a white solid.

Example 4: Analytical HPLC Method

The HPLC conditions are listed in Table 10 below:

TABLE 10

HPLC Conditions

| | |
|---|---|
| Column | Develosil ODS-UG-5, 5 μm, 250 mm × 4.6 mm, or equivalent |
| Guard column | Develosil ODS-UG-5, 5 μm, 10 mm × 4.0 mm, or equivalent |
| Column temperature | 45° C. ± 2° C. |
| Mode | Gradient |
| Mobile phase A | 50 mM Sodium perchlorate monohydrate, pH 2.50 |
| Mobile phase B | 63 mM Sodium perchlorate monohydrate, pH 2.50:$CH_3CN$ 80:20 |

| | Time (min) | % A | % B |
|---|---|---|---|
| Gradient | 0.0 | 97.5 | 2.5 |
| | 3.0 | 73.0$^a$ | 27.0$^a$ |
| | 33.0 | 68.0$^a$ | 32.0$^a$ |
| | 63.0 | 0.0 | 100 |
| | 88.0 | 0.0 | 100 |
| | 88.1 | 97.5 | 2.5 |
| | 105.0 | 97.5 | 2.5 |

| | |
|---|---|
| Flow rate | 1.0 mL/minute |
| Detection | UV at 254 nm (ceftolozane and ceftolozane related degradants) |
| Auto-sampler temperature | 4° C. ± 2° C. |
| Injection volume | 10 μL |
| Run time | 105 minutes |

$^a$The ratio of mobile phase A to mobile phase B may be adjusted to achieve the desired retention time. The change from 3.0 to 33.0 minutes must be an increase of 5.0% mobile phase B. For example, if the mobile phase B % is set at 27.5% at 3.0 minutes, the mobile phase B % must be set at 32.5% at 33.0 min.

Ceftolozane Sample Preparation

Samples should be prepared after the Blank and the System Suitability of the sequence are complete. The samples of ceftolozane were equilibrated to room temperature before dilution with the diluent described above.

System Suitability

At the beginning of each run, the diluent blank and SST are each injected in singlet. The system suitability is determined using the SST. The tailing factor for the ceftolozane peak should be between 0.8 and 1.5, and the retention time for the ceftolozane peak should be 24.0 minutes±1.0 minutes. The binary pump setting between 3.0 and 33.0 minutes may be adjusted to achieve the ceftolozane peak retention time. Each sample is prepared in singlet and injected twice.

Integration and Calculations

Only impurities >LOD (0.008% Area) are integrated. The peak area percentage for each impurity >LOD is taken directly from the chromatogram.

Limits:

| LOD (Area %)* | LOQ (Area %)* |
|---|---|
| 0.008% | 0.03% |

*Based on an actual area % from the chromatogram

The mean % area of each peak is calculated and the absolute difference of any peak in the two replicates cannot be >0.030%. The purity and related substances are determined based on relative area % of each peak with respect to the total peak area of the sample. The total impurities are the sum of the individual impurities >LOD. The calculations are as follows:

$$\% \text{ Impurity (\% Area)} = \frac{\text{Area}_{Impurity}}{\text{Area}_{Total}} \times 100\%$$

Where:

$\text{Area}_{impurity}$ = Area of the Individual Impurity Peak $\text{Area}_{Total}$ = Total Area of all peaks > LOD including Ceftolozane $$\text{Purity (\% Area)} = \frac{\text{Area}_{Ceftolozane}}{\text{Area}_{Total}} \times 100\%$$

Where:

$\text{Area}_{Ceftolozane}$ = Area of the Ceftolozane Peak $\text{Area}_{Total}$ = Total Area of all peaks≥LOD including Ceftolozane Total Impurities (% Area)=100−Purity (% Area)

The peaks of ceftolozane related degradants may be identified on the basis of the following RT and RRT values listed in Table 11. The RRT equals (Peak RT)/(Ceftolozane RT).

TABLE 11

Ceftolozane-related substances identified in ceftolozane sulfate drug substance

| Peak | Approximate Retention Time (min.) | Approximate RRT to Ceftolozane |
|---|---|---|
| Peak 1 | 4.1 | 0.17 |
| Peak 2a | 6.7 | 0.28 |
| Peak 2b | 7.5 | 0.30 |
| Peak 2c | 12.0 | 0.48 |
| Peak 3 | 12.4 | 0.51 |
| Peak 4 | 16.1 | 0.66 |
| Peak 5 | 21.8 | 0.89 |

TABLE 11-continued

Ceftolozane-related substances identified in ceftolozane sulfate drug substance

| Peak | Approximate Retention Time (min.) | Approximate RRT to Ceftolozane |
|---|---|---|
| Peak 7 | 30.1 | 1.2 |
| Peak 9 | 41.7 | 1.7 |

Example 5: Origin, Fate, and Control of Method 1 Related Substances

Studies were undertaken to identify process impurities and determine the fate of process components.

The following structurally-related substances can be observed in both ceftolozane TFA crude and ceftolozane sulfate drug substance: Peak 9, Peak 7, Peak 5, Peak 1, Peak 2a, Peak 2b, Peak 3 and Peak 4 (See Table 12, entries 5, 6, 7, 8, 9, 10, 11 and 12, respectively). Peak 2c is specified in ceftolozane sulfate drug substance (Table 12, entry 19).

The following ceftolozane related substances do not occur in the drug substance above the HPLC LOQ of 0.03% (for some impurities, other techniques were used to reach lower LOQs): Peak 10, TATD-OH, t-butyl ceftolozane, Peak 11, TATD-CLE/ACLE/UBT lactam and TATD-CLE/ACLE/UBT.

TABLE 12

List of Starting Materials and Process-Related Substances

| Entry | Substance/Formula/MW/CAS Number/Origin | Fate | Cumulative Purging Factor |
|---|---|---|---|
| 1 | UBT<br>$C_{31}H_{36}N_6O_3$<br>MW = 540.7<br>CAS Number: 689293-69-4 | Converted to ceftolozane; unreacted converted to Peak 1 | $2.71 \times 10^7$ |
| 2 | TATD-CLE<br>$C_{28}H_{33}ClN_6O_3S_2$<br>MW = 681.2<br>CAS Number: 689294-28-8 | Converted to TATD-IE; unreacted converted to impurities Peak 4, TATD-OH, Peak 10 | $1.35 \times 10^8$ |

TABLE 12-continued

List of Starting Materials and Process-Related Substances

| Entry | Substance/Formula/MW/CAS Number/Origin | Fate | Cumulative Purging Factor |
|---|---|---|---|
| 3 | TATD-IE<br>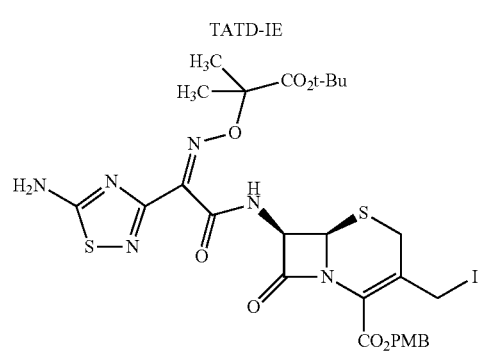<br>$C_{28}H_{33}IN_6O_8S_2$<br>MW = 772.6 | Converted to ceftolozane; unreacted converted to impurities Peak 4, TATD-OH, Peak 10 | 1.48 × $10^8$ |
| 4 | TATD-QUATE<br>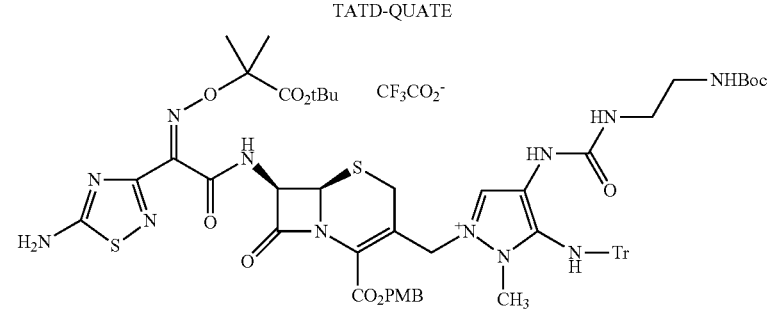<br>$C_{59}H_{69}N_{12}O_{11}S_2^+$<br>MW = 1185.5 (free base) | Converted to ceftolozane and tert-butyl ceftolozane | 9.99 × $10^9$ |
| 5 | Peak 9; RRT 1.66<br>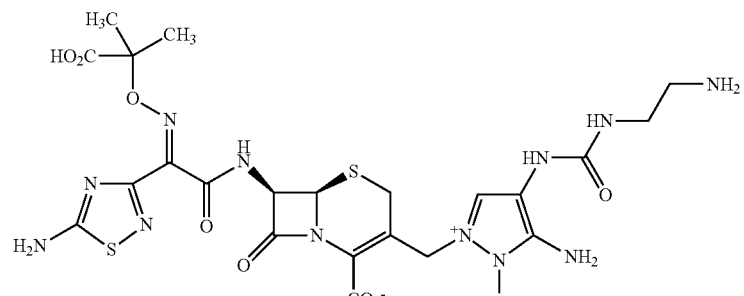<br>$C_{23}H_{30}N_{12}O_8S_2$<br>MW = 666.7 | Purged during filtration through hydrophobic resin and isolation in Method 2 | 12 |

TABLE 12-continued
List of Starting Materials and Process-Related Substances
| Entry | Substance/Formula/MW/CAS Number/Origin | Fate | Cumulative Purging Factor |
|---|---|---|---|
| 6 | Peak 7; RRT 1.24 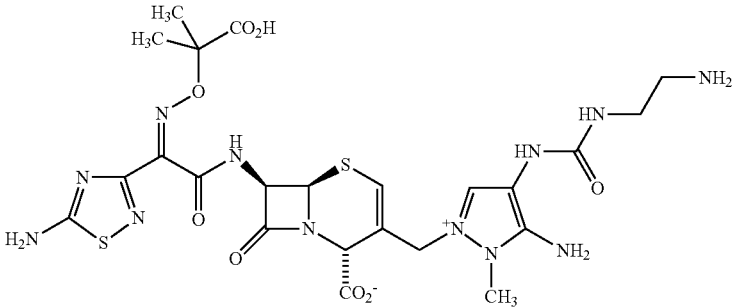 C₂₃H₃₀N₁₂O₈S₂ MW = 666.7 | Detected in Method 1 | 1 |
| 7 | Peak 5; RRT 0.89 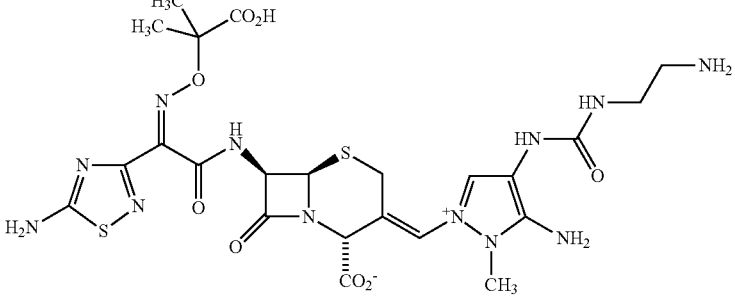 C₂₃H₃₀N₁₂O₈S₂ MW = 666.7 | Detected in Method 1 | 1 |
| 8 | Peak 1; RRT 0.17 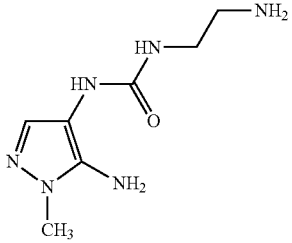 C₇H₁₄N₆O MW: 198.2 | Removed in Method 2, nanofiltration and isolation | 20 |

TABLE 12-continued

List of Starting Materials and Process-Related Substances

| Entry | Substance/Formula/MW/CAS Number/Origin | Fate | Cumulative Purging Factor |
|---|---|---|---|
| 9 | Peak 2a; RRT 0.28<br>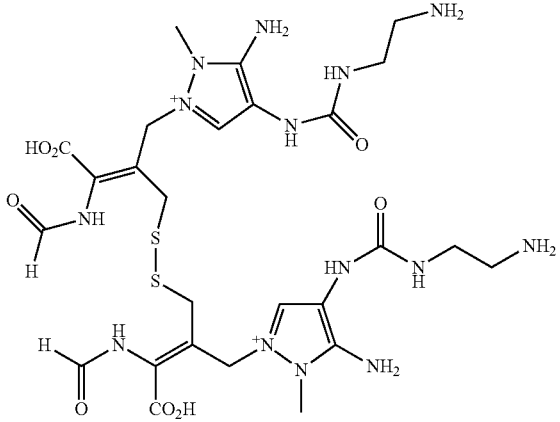<br>$C_{26}H_{42}N_{14}O_8S_2^{2+}$<br>MW = 742.8 | Purged in Method 2 | 3 |
| 10 | Peak 2b; RRT 0.30<br>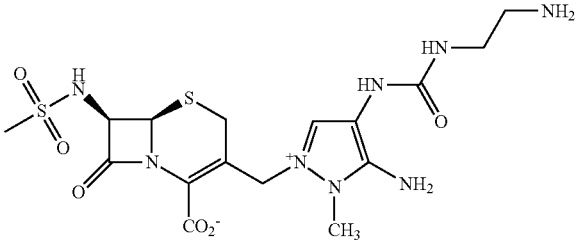<br>$C_{16}H_{24}N_8O_6S_2$<br>MW = 488.5 | Purged in Method 2 | Not determined |
| 11 | Peak 3; RRT 0.51<br>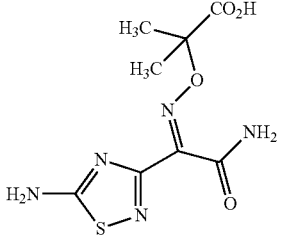<br>$C_8H_{11}N_5O_4S$<br>MW = 273.3 | Purged during nanofiltration and isolation in Method 2 | 4 |

TABLE 12-continued

List of Starting Materials and Process-Related Substances

| Entry | Substance/Formula/MW/CAS Number/Origin | Fate | Cumulative Purging Factor |
|---|---|---|---|
| 12 | Peak 4; RRT 0.66 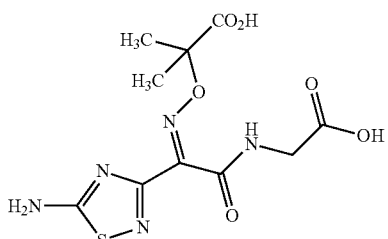 $C_{10}H_{13}N_5O_6S$ MW = 331.3 | Purged during isolation in Stage 3 | 6 |
| 13 | Peak 10; RRT 2.19 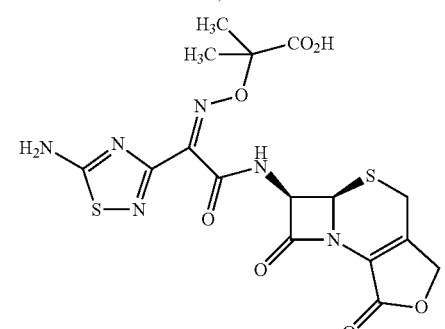 $C_{16}H_{16}N_6O_7S_2$ MW = 468.5 | Removed during filtration through the hydrophobic resin in Method 2 | Not determined |
| 14 | TATD-OH 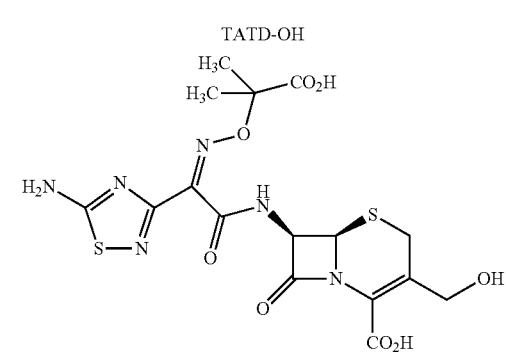 $C_{16}H_{18}N_6O_8S_2$ MW = 486.5 | Converted to Peak 10 in Method 2 and removed by filtration through hydrophobic resin in Method 2 | Not determined |

TABLE 12-continued

List of Starting Materials and Process-Related Substances

| Entry | Substance/Formula/MW/CAS Number/Origin | Fate | Cumulative Purging Factor |
|---|---|---|---|
| 15 | t-Butyl Ceftolozane (RRT 3.04) 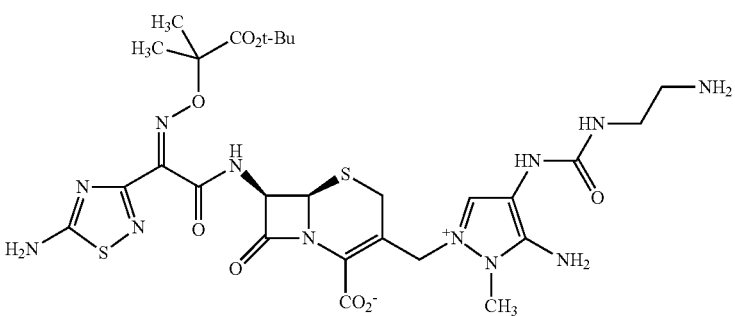 $C_{27}H_{38}N_{12}O_8S_2$ MW = 722.8 | Process intermediate removed by filtration through hydrophobic resin and isolation in Method 2 | 2,250 |
| 16 | Peak 11; RRT 2.21 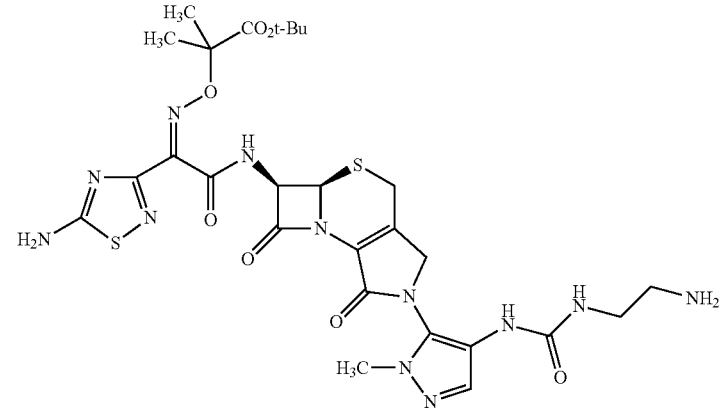 $C_{27}H_{36}N_{12}O_7S_2$ MW = 704.8 | Removed by filtration through hydrophobic resin in Method 2 | Not determined |
| 17 | TATD-CLE/ACLE/UBT lactam 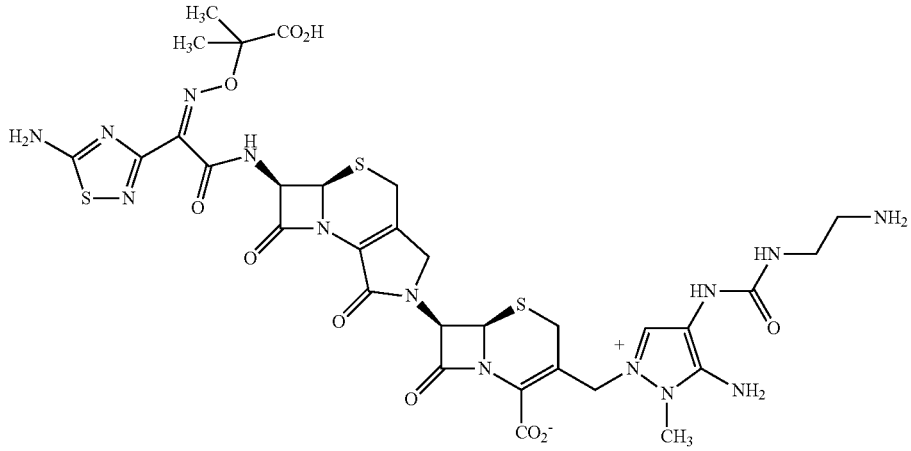 $C_{31}H_{36}N_{14}O_{10}S_3$ MW = 860.9 | Purged in Method 2 | 221 |

TABLE 12-continued

List of Starting Materials and Process-Related Substances

| Entry | Substance/Formula/MW/CAS Number/Origin | Fate | Cumulative Purging Factor |
|---|---|---|---|
| 18 | TATD-CLE/ACLE/UBT 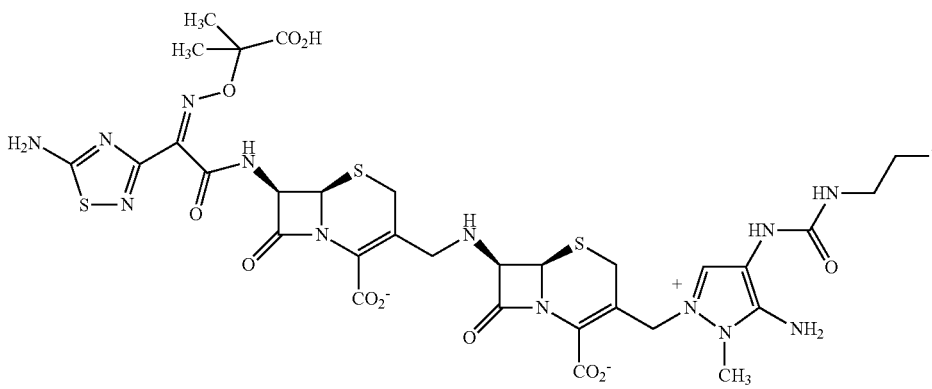 $C_{31}H_{37}N_{14}O_{11}S_3^-$ MW = 877.9 | Converted to TATD-CLE/ACLE/UBT lactam (entry 17) and purged in Method 2 | 1.8 |
| 19 | Peak 2c, RRT 0.48 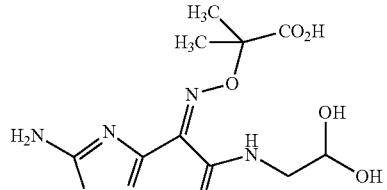 $C_{10}H_{15}N_5O_6S$ MW = 333.3 | Derived from a degradation pathway common to cephalosporins; removed in Method 2 | Not determined |

8. EMBODIMENTS

1. A method of making compound (V):

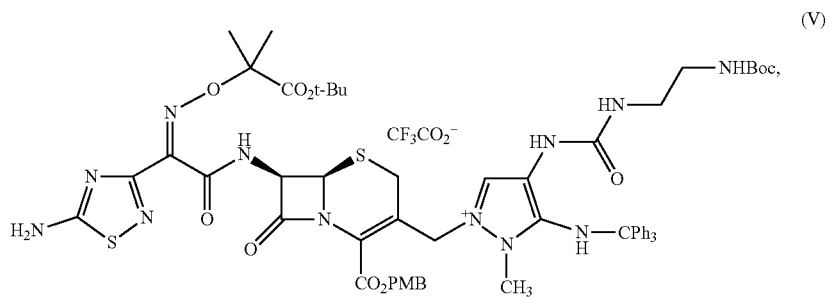

(V)

comprising the step of: (a) reacting compound (III):

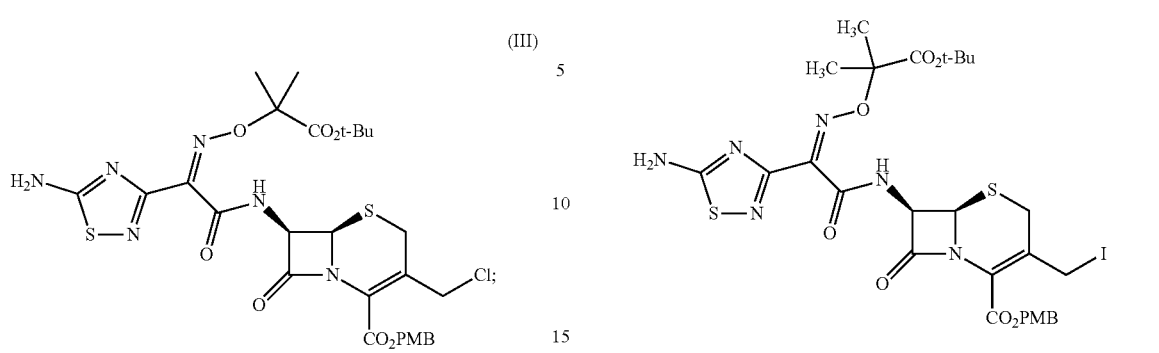

with compound (IV):

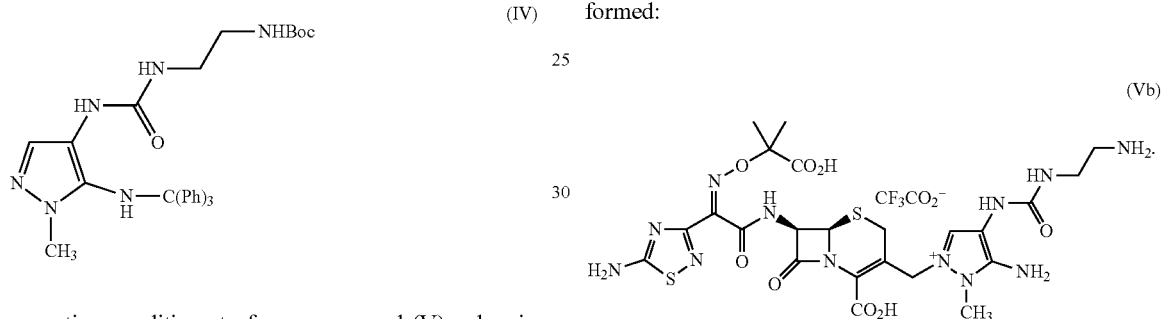

under reaction conditions to form compound (V), wherein the ratio of compound (IV) to compound (III) in step (a) is about 1.2:1.

2. The method of Embodiment 1, wherein step (a) comprises agitating a mixture of compound (IV), N-methylpyrrolidone, compound (III), potassium iodide and 1,3-bis(trimethylsilyl)urea at a temperature of between about 25 and 32° C.

3. The method of Embodiment 1 or 2, further comprising formation of compound (IIIa):

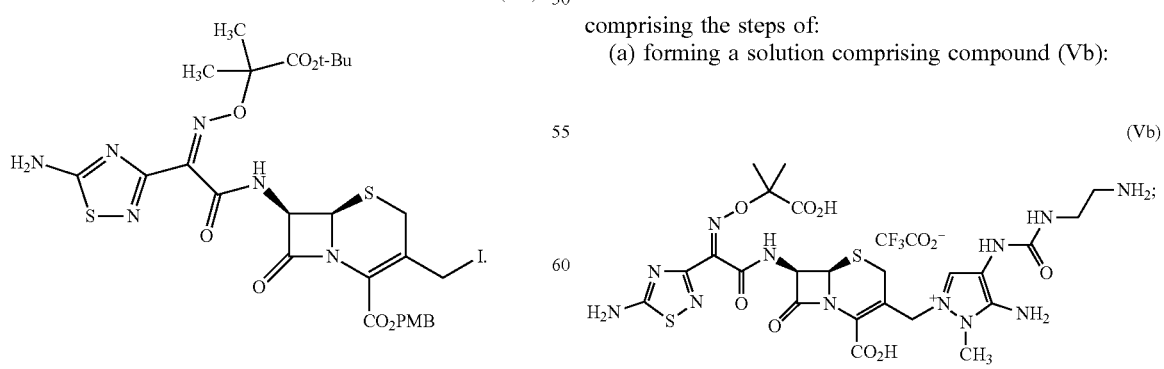

4. The method of any one of Embodiments 1 to 3, wherein the method results in a composition comprising compound (IIIa):

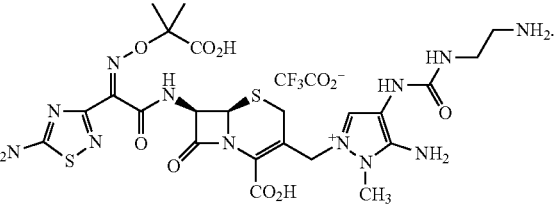

wherein the percentage of compound (IIIa) is less than about 5.0% with respect to compound (V) as measured by high performance liquid chromatography.

5. The method of any one of Embodiments 1-4, wherein the method further comprises (b) treating the compound (V) with trifluoroacetic acid, such that compound (Vb) is formed:

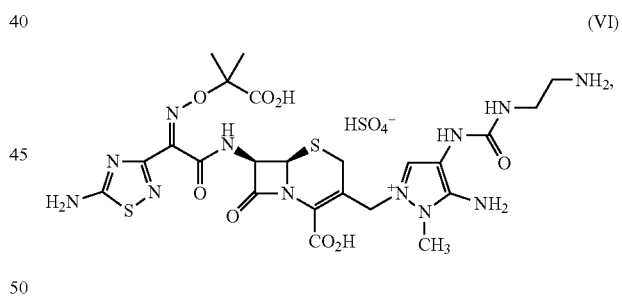

6. A method of making the compound (VI):

(VI)

comprising the steps of:
(a) forming a solution comprising compound (Vb):

(Vb)

(b) adjusting the pH of the solution to between 1.2 and 2.0 and removing insoluble material;

(c) filtering the resulting solution of step (b) through a resin; and (d) adding sulfuric acid to obtain compound (VI).

7. The method of Embodiment 6, wherein step (b) comprises adding hydrochloric acid to adjust the pH of the solution to between 1.2 and 2.0.

8. The method of Embodiment 6 or 7, wherein the resin of step (c) is a hydrophobic resin.

9. The method of any one of Embodiments 5-8, wherein the molar ratio of sulfuric acid added in step (d) is about 2.5:1 with respect to compound (Vb).

10. The method of any one of Embodiments 5-9, wherein the compound (Vb) is obtained by a process comprising the following steps:

(i) reacting compound (III):

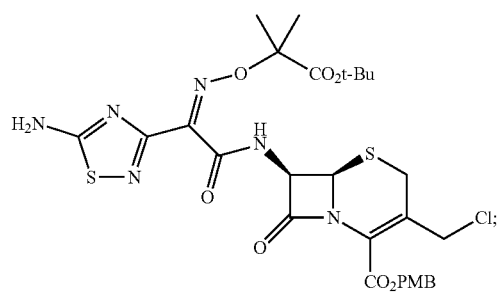

(III)

with compound (IV):

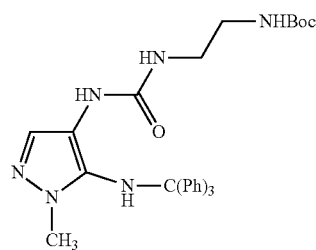

(IV)

under reaction conditions to form compound (V):

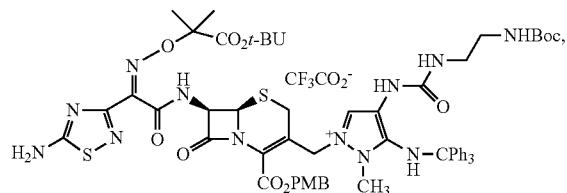

(V)

wherein the ratio of compound (IV) to compound (III) in step (a) is about 1.2:1; and (ii) treating compound (V) with trifluoroacetic acid, such that compound (Vb) is formed:

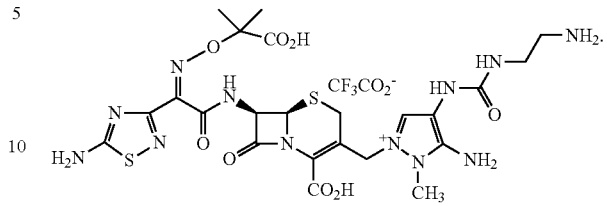

(Vb)

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A process of making a compound of formula (V'):

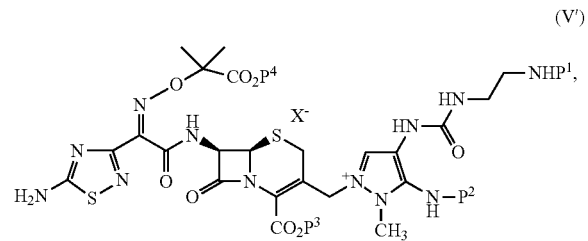

(V')

comprising admixing a compound of formula (III'):

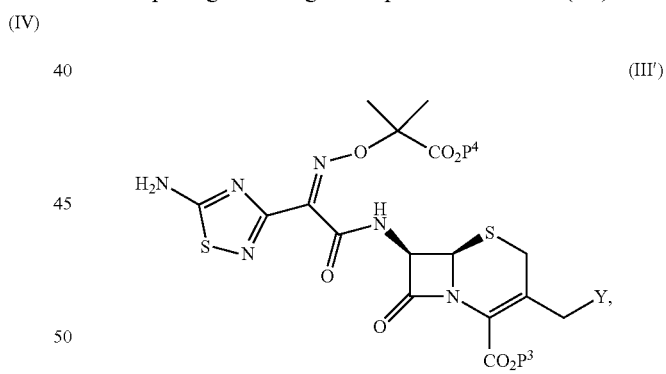

(III')

and a compound of formula (IV'):

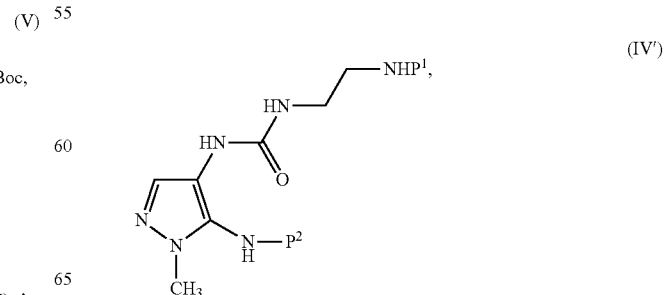

(IV')

in a solvent to provide the compound of formula (V'), wherein:
P¹ and P² are each independently an acid-labile nitrogen protecting group,
P³ and P⁴ are each independently an acid-labile oxygen protecting group,
X⁻ is a pharmaceutically acceptable salt,
Y is Cl or Br;
the molar ratio of the compound of formula (IV') to the compound of formula (III') is from 1.0:1 to 1.3:1; and
the solvent is purged with nitrogen at from 0.2 m³/h to 1.2 m³/h per kilogram of the compound of formula (III').

2. A process of making a compound of formula (V'):

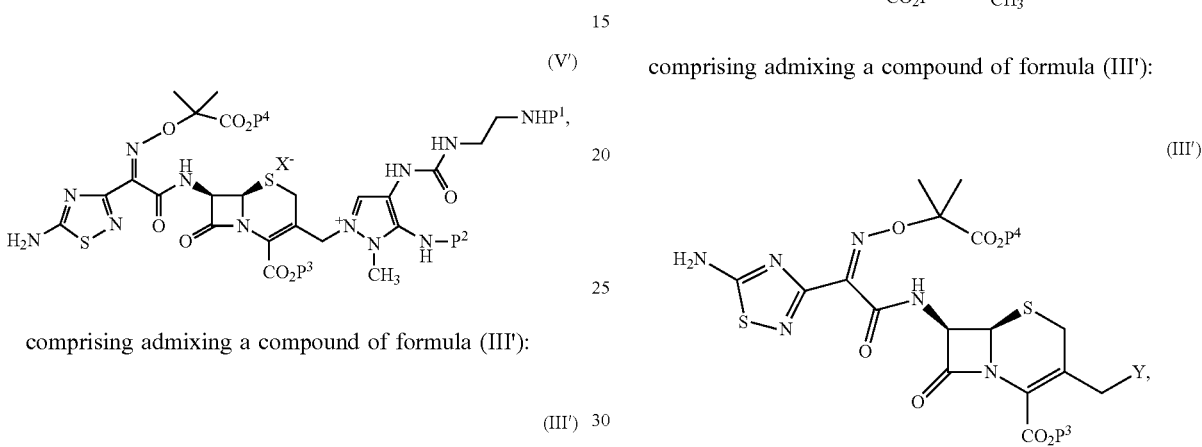

comprising admixing a compound of formula (III'):

and a compound of formula (IV'):

in a solvent to provide the compound of formula (V'), wherein:
P¹ and P² are each independently an acid-labile nitrogen protecting group,
P³ and P⁴ are each independently an acid-labile oxygen protecting group,
X⁻ is a pharmaceutically acceptable salt,
Y is Cl, Br or I;
the temperature of the admixture is from 25° C. to 32° C.; and the solvent is purged with nitrogen at from 0.2 m³/h to 1.2 m³/h per kilogram of the compound of formula (III').

3. A process of making a compound of formula (V'):

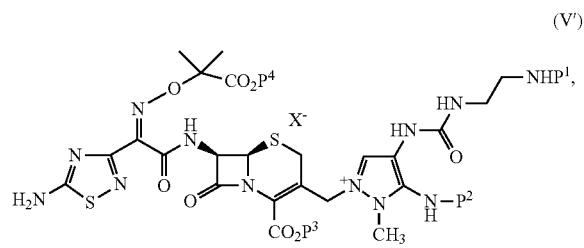

comprising admixing a compound of formula (III'):

and a compound of formula (IV'):

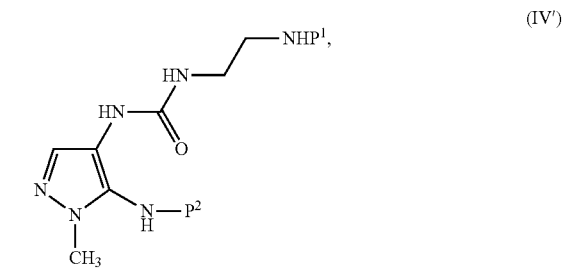

in a solvent to provide the compound of formula (V'), wherein:
P¹ and P² are each independently an acid-labile nitrogen protecting group,
P³ and P⁴ are each independently an acid-labile oxygen protecting group,
X⁻ is a pharmaceutically acceptable salt,
Y is Cl, Br or I; and
the solvent is purged with nitrogen at from 0.2 m³/h to 1.2 m³/h per kilogram of the compound of formula (III').

4. The process of claim 1, 2 or 3, wherein P¹ is tert-butoxycarbonyl.

5. The process of claim 1, 2 or 3, wherein P² is triphenylmethyl.

6. The process of claim 1, 2 or 3, wherein P³ is 4-methoxybenzyl.

7. The process of claim 1, 2 or 3, wherein P⁴ is tert-butyl.

8. The process of claim 1, 2 or 3, wherein X⁻ is trifluoroacetate, bromide, chloride, iodide, or methanesulfonate.

9. The process of claim 1, 2 or 3, wherein Y is Cl.

10. The process of claim 1, 2 or 3, wherein the admixture further comprises 1, 3-bis(trimethylsilyl)urea.

11. The process of claim 1, 2 or 3, wherein the admixture further comprises potassium iodide.

12. The process of claim 1, 2 or 3, wherein the temperature is from 27° C. to 30° C.

13. The process of claim 1, 2 or 3, wherein the solvent is a polar aprotic solvent.

14. The process of claim 1, 2 or 3, wherein the solvent comprises N-methylpyrrolidinone.

15. The process of claim 1, 2 or 3, wherein the solvent is purged with nitrogen at from 0.3 m³/h to 1.2 m³/h per kilogram of the compound of formula (III').

16. The process of claim 1, 2 or 3, wherein the molar ratio of the compound of formula (IV') to the compound of formula (III') is 1.2:1.

17. The process of claim 1, 2 or 3, wherein the compound of formula (V') has the structure of compound (V):

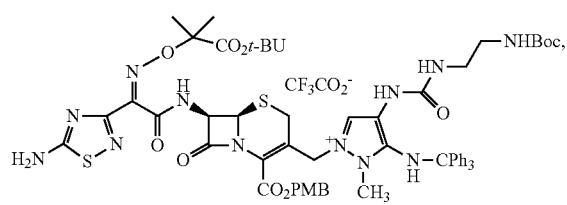
(V)

the compound of formula (III') has the structure of compound (III):

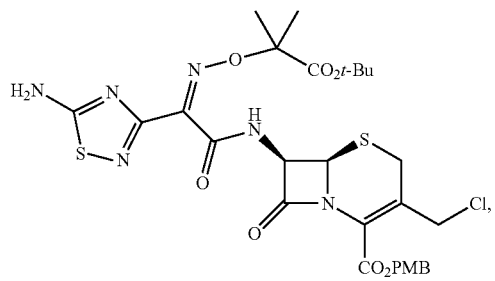
(III)

and the compound of formula (IV') has the structure of compound (IV):

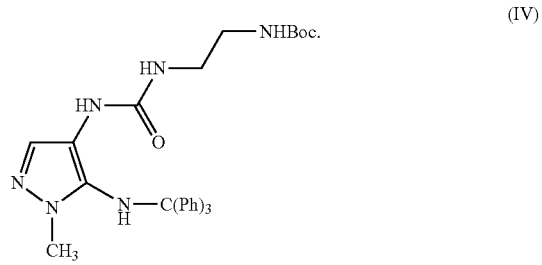
(IV)

18. The process of claim 1, 2 or 3, further comprising making a compound of formula (Vb'):

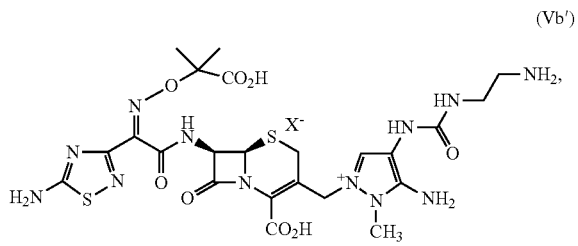
(Vb')

comprising contacting the compound of formula (V') with an acid of formula HX,
at a temperature of from 18° C. to 22° C.,
to provide the compound of formula (Vb'),
wherein
HX is trifluoroacetic acid, hydrogen bromide, hydrogen chloride, hydrogen iodide, or methanesulfonic acid; and
X' is trifluoroacetate, bromide, chloride, iodide, or methanesulfonate.

19. The process of claim 18, wherein the amount of the acid is from 4.5 L to 6.0 L per kilogram of the compound of formula (V').

20. The process of claim 18, further comprising separating the compound of formula (Vb') at a temperature of from −40° C. to −30° C.

* * * * *